United States Patent [19]
Williams

[11] Patent Number: 5,616,482
[45] Date of Patent: Apr. 1, 1997

[54] CHIMERIC TOXINS

[76] Inventor: Diane Williams, 22 Danforth Way, Franklin, Mass. 02038

[21] Appl. No.: 231,397

[22] Filed: Apr. 22, 1994

Related U.S. Application Data

[63] Continuation of Ser. No. 886,715, May 21, 1992, abandoned, which is a continuation of Ser. No. 537,430, Jun. 13, 1990, abandoned, which is a continuation-in-part of Ser. No. 488,608, Mar. 2, 1990, abandoned.

[51] Int. Cl.⁶ .............................. C12N 9/12; C07K 14/34; C07K 14/52
[52] U.S. Cl. ...................... 435/194; 530/350; 530/351; 935/47
[58] Field of Search ................... 530/350, 351; 935/47; 435/194

[56] References Cited

U.S. PATENT DOCUMENTS

| 4,468,382 | 8/1984 | Bacha .......................... 424/177 |
| 4,675,382 | 6/1987 | Murphy ........................ 530/350 |
| 4,830,962 | 5/1989 | Gelfand et al. ............... 435/68 |

FOREIGN PATENT DOCUMENTS

| 259904 | 3/1988 | European Pat. Off. . |
| 332174 | 9/1989 | European Pat. Off. . |
| 8503508 | 9/1985 | WIPO . |
| 8702987 | 5/1987 | WIPO . |
| 9119745 | 12/1991 | WIPO . |

OTHER PUBLICATIONS

Edwards et al., Mol. Cell Biol. 9(7):2860–67 (1989).
Lambotte et al., J. Cell Biol. 87:837–40 (1980).
Colombatti et al., J. Biol. Chem. 261(7):3030–35 (1986).
Greenfield et al., PNAS USA 80:6853–57 (1983).
Boquet et al., PNAS USA 73:4449–53 (1976).
Bacha et al., J. Biol. Chem. 258(3):1565–70 (1983).
Cabiaux et al., J. Biol. Chem. 264(9):4928–38 (1989).
Rappuoli et al., J. Bacteriol. 153:1202–10 (1983).
Bacha et al., J. Exp. Med. 167:612–22 (1988).
Williams et al., in Protein Engineering 1:493–98 (1987).
Bishai et al., J. Bacteriol. 169(4):1554–63 (1987).
D. Williams et al., "Structure/Function Analysis of IL–2 Toxin," in Protein Society Meeting, Aug. 1989, Abstract T 71.
Greenfield, et al., Science 238:536–39 (1987).
Simpson et al., Cell, vol. 29, Jun. 1982, pp. 469–473.

Primary Examiner—Robert A. Wax
Assistant Examiner—Keith D. Hendricks
Attorney, Agent, or Firm—Lerner, David, Littenberg, Krumholz & Mentlik

[57] ABSTRACT

A chimeric diptheria toxin comprising protein fragments joined together by peptide bonds.

33 Claims, 11 Drawing Sheets

FIG. 1A

ARG 190 — CYS₁₈₆ ............................................ GLY₁ – NH₂

ARG 192 — S–S  346    371

ARG 193 — CYS₂₀₁ ............ CYS₄₆₁

↑ FRAGMENT B →

TRANS-MEMBRANE REGION    S–S

COOH – SER₅₃₅ — ▓▓▓▓▓▓ CYS₄₇₁

↑ TOXIN RECEPTER BINDING DOMAIN

| SphI<br>GCATGCT<br>CGTACGA | Asn<br>AAC<br>TTG | Ser<br>AGC<br>TCG | Asp<br>GAC<br>CTG | Ser<br>AGC<br>TCG | Glu<br>GAA<br>CTT | Cys<br>TGT<br>ACA | Pro<br>CCG<br>GGC | Leu<br>CTG<br>GAC | Ser<br>AGC<br>TCG | His<br>CAC<br>GTG | Asp<br>GAC<br>CTG | Gly<br>GGT<br>CCA |
| --- | --- | --- | --- | --- | --- | --- | --- | --- | --- | --- | --- | --- |
| Tyr<br>TAC<br>ATG | Cys<br>TGT<br>ACA | Leu<br>CTG<br>GAC | His<br>CAC<br>GTG | Asp<br>GAC<br>CTG | Gly<br>GGT<br>CCA | Val<br>GTT<br>CAA | Cys<br>TGT<br>ACA | Met<br>ATG<br>TAC | Tyr<br>TAC<br>ATG | Ile<br>ATC<br>TAG | Glu<br>GAA<br>CTT | Ala<br>GCT<br>CGA |
| Leu<br>CTA<br>GAT | Asp<br>GAC<br>CTG | Lys<br>AAA<br>TTT | Tyr<br>TAC<br>ATG | Ala<br>GCT<br>CGA | Cys<br>TGT<br>ACA | Asn<br>AAC<br>TTG | Cys<br>TGT<br>ACA | Val<br>GTT<br>CAA | Gly<br>GGT<br>CCA | Ile<br>ATC<br>TAG | Tyr<br>TAC<br>ATG | |
| Gly<br>GGT<br>CCA | Glu<br>GAA<br>CTT | Arg<br>CGC<br>GCG | Cys<br>TGT<br>ACA | Gln<br>CAG<br>GTC | Tyr<br>TAC<br>ATG | Arg<br>CGC<br>GCG | Asp<br>GAC<br>CTG | Val<br>GTT<br>CAA | Gly<br>GGT<br>CCA | Trp<br>TGG<br>ACC | Trp<br>TGG<br>ACC | |
| Leu<br>CTG<br>GAC | Arg<br>CGC<br>GCG | | | | | | | Asp<br>GAC<br>CTG | Leu<br>CTG<br>GAC | Lys<br>AAA<br>TTT | | |

<u>STOP</u>
TGAAGTACTAATTTACGTACCGGAGGCCTAAGGAGCCC
<u>ACTTC</u>ATGATTAAATGCATGGCCTCCGGATTCCTCGGG

<u>TrpA TERMINATOR</u>     <u>HindIII</u>
GCCTAATGAGCGGGCTTTTTTTCCGTCGACAAGGCCTGAACGTCGAAGCTT
CGGATTACTCGCCCGAAAAAAAGGCAGCTGTTCCGGACTTGCAGCTTCGAA

CHIMERIC TOXINS

This is a continuation of application Ser. No. 07/886,715 filed on May 21, 1992, which is a continuation of application Ser. No. 07/537,430, filed on Jun. 13, 1990, which is a continuation-in-part of 07/488,608 filed on Mar. 2, 1990, all now abandoned.

BACKGROUND OF THE INVENTION

This invention relates to the use of recombinant DNA techniques to construct chimeric toxin molecules.

The literature contains many examples of fused genes which code for chimeric proteins. For example, Villa-Komaroff et al. (1978) Proc. Natl. Acad. Sci. U.S.A. 75:3727–3731, describes a fused gene made up of a eukaryotic structural gene fused to a non-cytoplasmic bacterial gene. The fused gene codes for a chimeric protein which is transported out of the cytoplasm. Murphy U.S. Pat. No. 4,675,382, hereby incorporated by reference, describes the use of recombinant DNA techniques to produce a hybrid, or chimetic, protein, consisting of a portion of the diphtheria toxin (DT) molecule linked via a peptide linkage to a cell-specific ligand such as α-melanocyte stimulating hormone (MSH). The DT-MSH chimetic toxin was selectively toxic for particular target cells, i.e., α-MSH receptor positive human malignant melanoma cells.

A diphtheria toxin-related fusion protein, $DAB_{486}$-IL-2, in which the native receptor binding domain of DT was genetically replaced with a portion of the polypeptide hormone interleukin-2 (IL-2) has been described in Williams et al. (1987) Protein Engineering 1:493–498, hereby incorporated by reference. $DAB_{486}$-IL-2 is a 68,142 Da fusion protein consisting of, in the following order: Met; DT residues 1–485; and amino acids 2 through 133 of mature human IL-2. $DAB_{486}$-IL-2 has been shown to bind to the IL-2 receptor and to selectively intoxicate lymphocytes which bear the high affinity form of the IL-2 receptor, Bacha et al. (1988) J. Exp. Med 167:612–622. Moreover, the cytotoxic action of $DAB_{486}$-IL-2, like that of native diphtheria toxin, requires receptor-mediated endocytosis, passage through an acidic compartment, and delivery of Fragment A associated ADP-ribosyltransferase to the cytosol of target cells, Bacha et al. (1988) supra.

SUMMARY OF THE INVENTION

In general, the invention features a chimeric toxin including protein fragments joined together by peptide bonds. The chimetic toxin includes, in sequential order, beginning at the amino terminal end of the chimeric toxin:

(a) the enzymatically active Fragment A of diphtheria toxin;

(b) a first fragment including the cleavage domain $1_1$ adjacent Fragment A of diphtheria toxin;

(c) a second fragment including at least a portion of the hydrophobic transmembrane region of Fragment B of diphtheria toxin, the second fragment also having a deletion, C-terminal to the transmembrane region, of at least 50, or more preferably of at least 80, diphtheria toxin amino acid residues, and the second fragment not including domain $1_2$; and (d) a third fragment including a portion of a cell-specific polypeptide ligand e.g., an interleukin (preferably interleukin 2, or, epidermal growth factor (EGF)), including at least a portion of the binding domain of the polypeptide ligand, that portion being effective to cause the chimeric toxin to bind selectively to a predetermined class of cells to be attacked by enzymatically active Fragment A.

In preferred embodiments the chimeric toxin possesses at least one of, and more preferably at least two of, and even more preferably at least three of: greater toxicity to receptor-bearing cells than that of an analagous $DAB_{486}$-containing-toxin (an analagous $DAB_{486}$-containing toxin is a toxin which is identical to the chimeric toxin of the preferred embodiment except that $DAB_{486}$ replaces the fragments of DT recited in (a), (b), and (c) above, i.e., a toxin consisting of $DAB_{486}$ fused to the fragment defined in (d) above); a lower $K_d$ (i.e., a greater binding affinity) for the receptor (i.e., the sites to which the third fragment (described above) binds on the cells to be attacked) than that of an analagous $DAB_{486}$-containing-toxin; greater resistance to proteolytic degradation than that of $DAB_{486}$-containing-toxin; greater resistance to the inhibition of its cytotoxicity by competitive inhibitors, e.g., the polypeptide of (d) above, than that exhibited by an analagous $DAB_{486}$-containing-toxin; the ability to inhibit protein synthesis in target cells to a given degree by a period of exposure that is shorter than the period of exposure required by an analagous $DAB_{486}$-containing-toxin to inhibit protein synthesis to the same degree; or the ability to effect a more rapid onset of the inhibition of protein synthesis than that seen in an analagous $DAB_{486}$-containing-toxin.

Other preferred embodiments include: chimeric toxins wherein the fragment of Fragment B of diphtheria toxin does not include any diphtheria toxin sequences between the hydrophobic transmembrane region and amino acid residues 484 or 485 of native diphtheria toxin; chimeric toxins lacking diphtheria toxin sequences C-terminal to amino acid residue 386 of native diphtheria toxin; and chimeric toxins including $DAB_{389}$ fused to the third fragment defined above.

Other preferred embodiments include: a chimeric toxin in which the portion of the polypeptide ligand is a portion of interleukin-2 effective to cause the chimeric toxin to bind to IL-2 receptor bearing cells, in particular, T cells; a chimetic toxin in which the portion of the polypeptide ligand is a portion of EGF effective to cause the chimeric toxin to bind to cells bearing the EGF receptor; the chimeric toxin $DAB_{389}$-IL-2; and the chimeric toxin $DAB_{389}$-EGF.

In other preferred embodiments in which the ligand is IL-2 or a portion thereof, the chimeric toxin possesses at least one of: greater toxicity to IL-2 receptor-bearing cells than that exhibited by $DAB_{486}$-IL-2, a lower $K_d$ for the IL-2 high affinity receptor than that of $DAB_{486}$-IL-2, or a greater resistance to proteolytic degradation than that exhibited by $DAB_{486}$-IL-2.

In other preferred embodiments in which the ligand is EGF or a portion thereof, the chimeric toxin posseses at least one of: greater toxicity to EGF-receptor-bearing cells than that exhibited by $DAB_{486}$EGF; a lower $K_d$ for the EGF receptor than that of $DAB_{486}$EGF, greater resistance to the inhibition of its cytotoxicity by competitive inhibitors, e.g., EGF, than that of $DAB_{486}$-EGF; the ability to inhibit protein synthesis in EGF receptor bearing cells to a given degree by a period of exposure that is shorter than the period of exposure required by $DAB_{486}$EGF to inhibit protein synthesis to the same degree; or the ability to effect a more rapid onset of the inhibition of protein synthesis in EGF-receptor-bearing cells than that seen in $DAB_{486}$EGF.

The chimeric toxins of the invention are preferably encoded by fused genes which include regions encoding the protein fragments of the chimeric toxin, DNA sequences encoding the chimeric toxins of the invention, expression vectors encoding those DNA sequences, cells transformed with those expression vectors, and methods of producing the chimeric toxins including culturing cells transformed with expression vectors containing DNA encoding the chimeric toxins and isolating the chimeric toxins from the cells or their supernatants.

Native diphtheria toxin, as used herein, means the 535 amino acid diphtheria toxin protein secreted by *Corynebacterium diphtheriae*. The sequence of an allele of the gene which encodes native diphtheria toxin can be found in Greenfield et al. (1983) Proc. Natl. Acad. Sci. USA 80:6853–6857, hereby incorporated by reference. Enzymatically active Fragment A, as used herein, means amino acid residues Gly 1 through Arg 193 of native DT, or an enzymatically active derivative or analog of the natural sequence. Cleavage domain $l_1$, as used herein, means the protease sensitive domain within the region, spanning Cys 186 and Cys 201 of native DT. Fragment B, as used herein, means the region from Ser 194 through Ser 535 of native DT. The hydrophobic transmembrane region of Fragment B, as used herein, means the amino acid sequence bearing a structural similarity to the bilayer-spanning helices of integral membrane proteins and located approximately at or derived from amino acid residue 346 through amino acid residue 371 of native diphtheria toxin. Domain $l_2$, as used herein, means the region spanning Cys 461 and Cys 471 of native DT. The generalized eukaryotic binding size of Fragment B, as used herein, means a region within the C-terminal 50 amino acid residues of native DT responsible for binding DT to its native receptor on the surface of eukaryotic cells. The chimeric toxins of the inventions do not include the generalized eukaryotic binding site of Fragment B.

Toxic or cytotoxic, as used herein, means capable of inhibiting protein synthesis in a cell, inhibiting cell growth or division, or killing a cell.

$DAB_{489}$ consists of, in the following order, methionine, and amino acid residues 1–485 of native DT.

$DAB_{389}$ consists of, in the following order, methionine, amino acid residues 1–386 of native DT, and amino acid residues 484–485 of native DT.

$DAB_{486}$-IL-2 is a fusion protein consisting of, in the following order, methionine, amino acid residues 1–485 of native DT, and amino acid residues 2–133 of IL-2. $DAB_{485}$-IL-2 is identical except that it lacks the initial methionine residue.

$DAB_{389}$-IL-2 consists of $DAB_{389}$ fused to amino acid residues 2–133 of IL-2.

$DAB_{389}$EGF consists of $DAB_{389}$ fused to EGF.

Receptor means the site to which the cell-specific polypeptide ligand (described in (d) above) binds.

Chimeric toxins of the invention display one or more of the following advantages: greater toxicity than that of an analagous $DAB_{486}$-containing toxin; a greater affinity for the receptor than that of an analagous $DAB_{486}$-containing toxin; when expressed in the cytoplasm of *E.coli*, greater resistance to proteolytic degradation than that exhibited by an analagous $DAB_{486}$-containing toxin; greater resistance to the inhibition of its cytotoxicity by competitive inhibitors, e.g., the polypeptide of (d) above, than that exhibited by an analagous $DAB_{486}$-containing toxin; the ability to inhibit protein synthesis in target cells to a given degree by a period of exposure that is shorter than the period of exposure required by an analagous $DAB_{486}$-containing-toxin to inhibit protein synthesis to the same degree; or the ability to effect a more rapid onset of the inhibition of protein synthesis than that seen in an analagous $DAB_{486}$-containing-toxin.

Aberrant expression of the epidermal growth factor receptor is a characteristic of several malignancies including those of the breast, bladder, prostate, lung and neuroglia. Chimeric toxins of the invention allow therapeutic targeting the cytotoxic action of diptheria toxin to EGF receptor positive tumor cells. In these chimeric toxins the sequences for the binding domain of diptheria toxin have been replaced by those for human EGF. These chimeric toxins inhibit protein synthesis by the same mechanism as diptheria toxin and are specifically cytotoxic for human tumor cells which express elevated levels of EGF receptors. The uptake of these chimeric toxins occur with kinetics which permit use of this molecule as a powerful therapeutic agent for treatment of malignancies characterized by EGF receptor expression.

Other features and advantages of the invention will be apparent from the following description of the preferred embodiments and from the claims.

DESCRIPTION OF THE PREFERRED EMBODIMENTS

The drawings will first be briefly described.

Drawings

FIGS. 1a and b are a diagram of the DT molecule and of various fusion proteins.

FIG. 6 is the sequence of a synthetic EGF gene.

Figure 2:
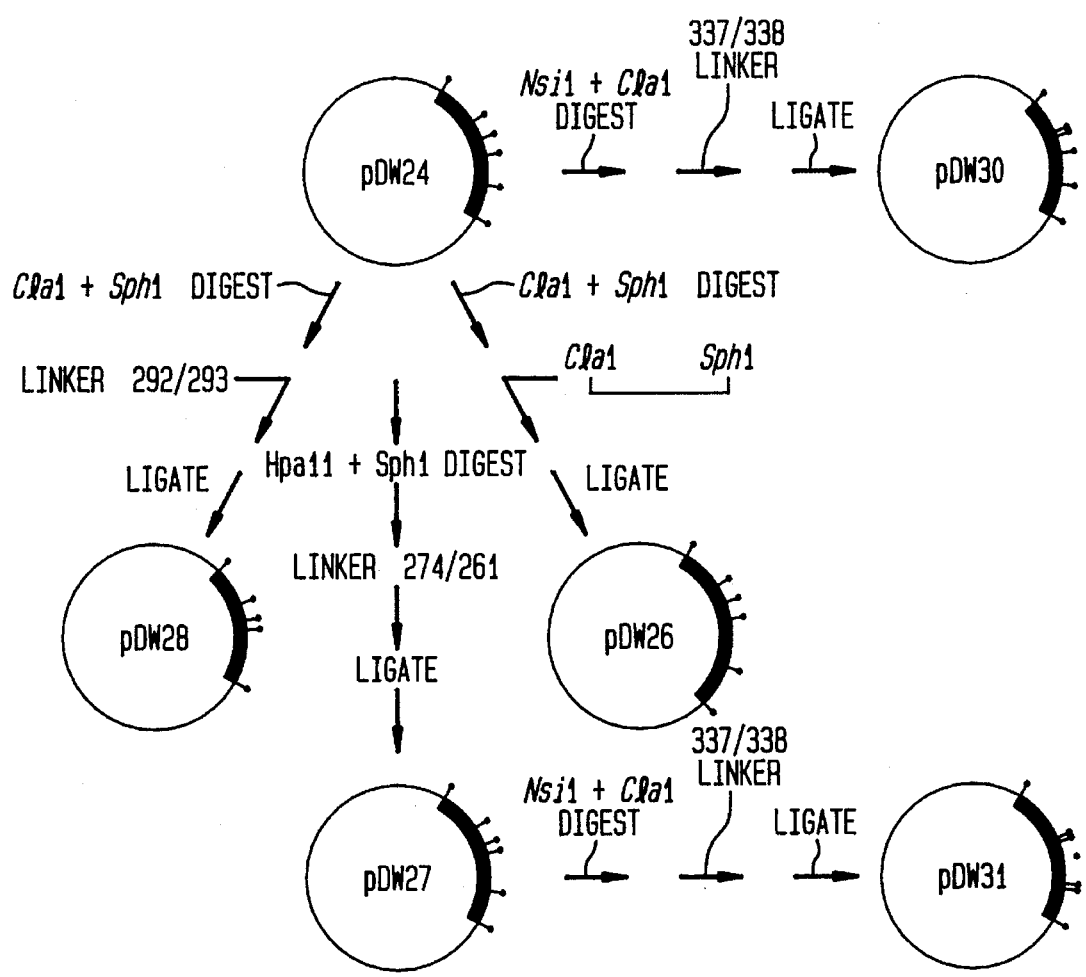
FIG. 2 is a depiction of the construction of the plasmids of a preferred embodiment.

Structure and Synthesis of chimeric toxin $DAB_{486}$-IL-2

Figure 1B:
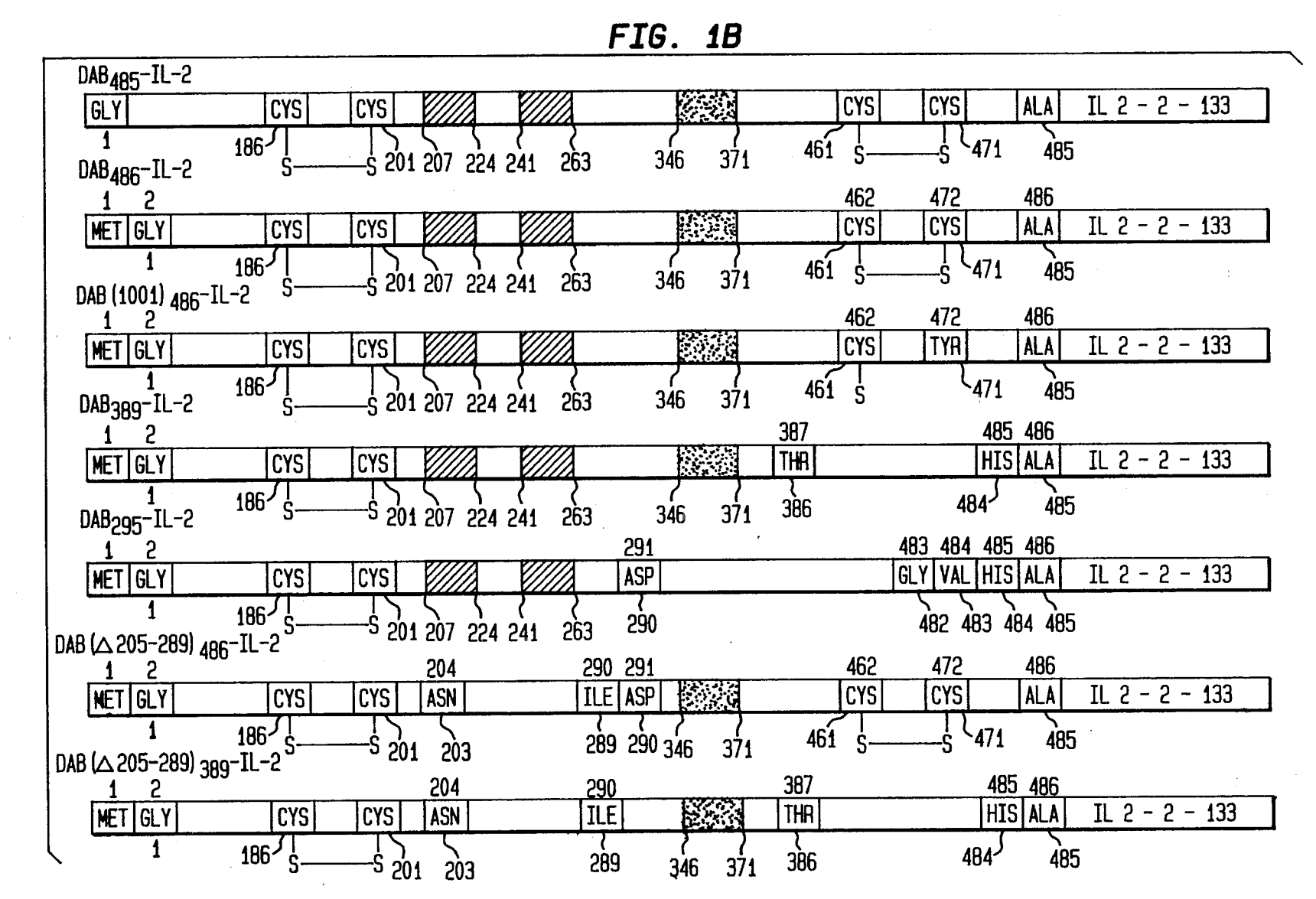

$DAB_{486}$-IL-2 is a chimeric toxin consisting of Met followed by amino acid residues 1 through 485 of mature DT fused to amino acid residues 2 through 133 of IL-2. The DT portion of the chimeric toxin $DAB_{486}$-IL-2 includes all of DT fragment A and the portion of DT fragment B extending to residue 485 of mature native DT. Thus $DAB_{486}$-IL-2 extends past the disulfide bridge linking Cys 461 with Cys 471. See FIG. 1a for the structure of DT. (The nomenclature adopted for IL-2-toxin is $DAB_{486}$-IL-2, where D indicates diphtheria toxin, A and B indicate wild type sequences for these fragments, and IL-2 indicates human interleukin-2 sequences. Mutant alleles are indicated by a number in parentheses following DAB. The numerical subscript indicates the number of DT-related amino acids in the fusion protein. Since the deletion of the tox signal sequence and expression from the trc promoter results in the addition of a methionine residue to the N-terminus, the numbering of DAB-IL-2 fusion toxins is +1 out of phase with that of native diphtheria toxin.)

pDW24, which carries $DAB_{486}$-IL-2 was constructed as follows. pUC18 (New England BioLabs) was digested with PstI and BglI and the PstI-BglI fragment carrying the *E.coli* origin of replication, the polylinker region, and the 3' portion of the β-lacatamase gene ($amp^r$) was recovered. Plasmid pKK-233-2 (Pharmacia) was digested with PstI and BglI and the PstI-BglI fragment carrying, two transcription terminators and the 5' portion of the β-lactamase gene was recovered. pDW22 was constructed by ligating these two recovered fragments together.

pDW23 was constructed by isolating a BamHI-SalI fragment encoding human IL-2 from plasmid pDW15 (Williams et al. (1988) Nucleic Acids Res. 16:10453–10467) and ligating it to BamHI/SalI digested pDW22 (described above).

pDW24 was constructed as follows. A BamHI-NcoI fragment carrying the trc promoter and translational initiation codon (ATG) was isolated from plasmid pKK233-2 (Pharmacia). The DNA sequence encoding amino acid residues 1 through 485 of DT was obtained by digesting pABC508 (Williams et al. (1987) Protein Engineering 1:493–498) with SphI and HaeII and recovering the HaeII-SphI fragment containing the sequence encoding amino acid residues 1 through 485 of DT. A NcoI/HaeII linker (5'CCATGGGCGC 3') was ligated to the HaeII-SphI fragment and that contruction was then ligated to the previously isolated BamHI-NcoI fragment carrying the trc promoter. This results in a Bam HI-SphI fragment bearing, in the following order, the trc promoter, the NcoI site (which supplies the ATG initiator codon for Met), and the sequence encoding residues 1 through 485 of native DT. This fragment was inserted into pDW23 that had been digested with Bam HI and SphI. The resulting plasmid was desigated pDW24. The fusion protein ($DAB_{486}$-Il-2) encoded by pDW24 is expressed from the trc promoter and consists of Met followed by amino acids 1 through 485 of mature DT fused to amino acids 2 through 133 of human IL-2.

Figure 3:
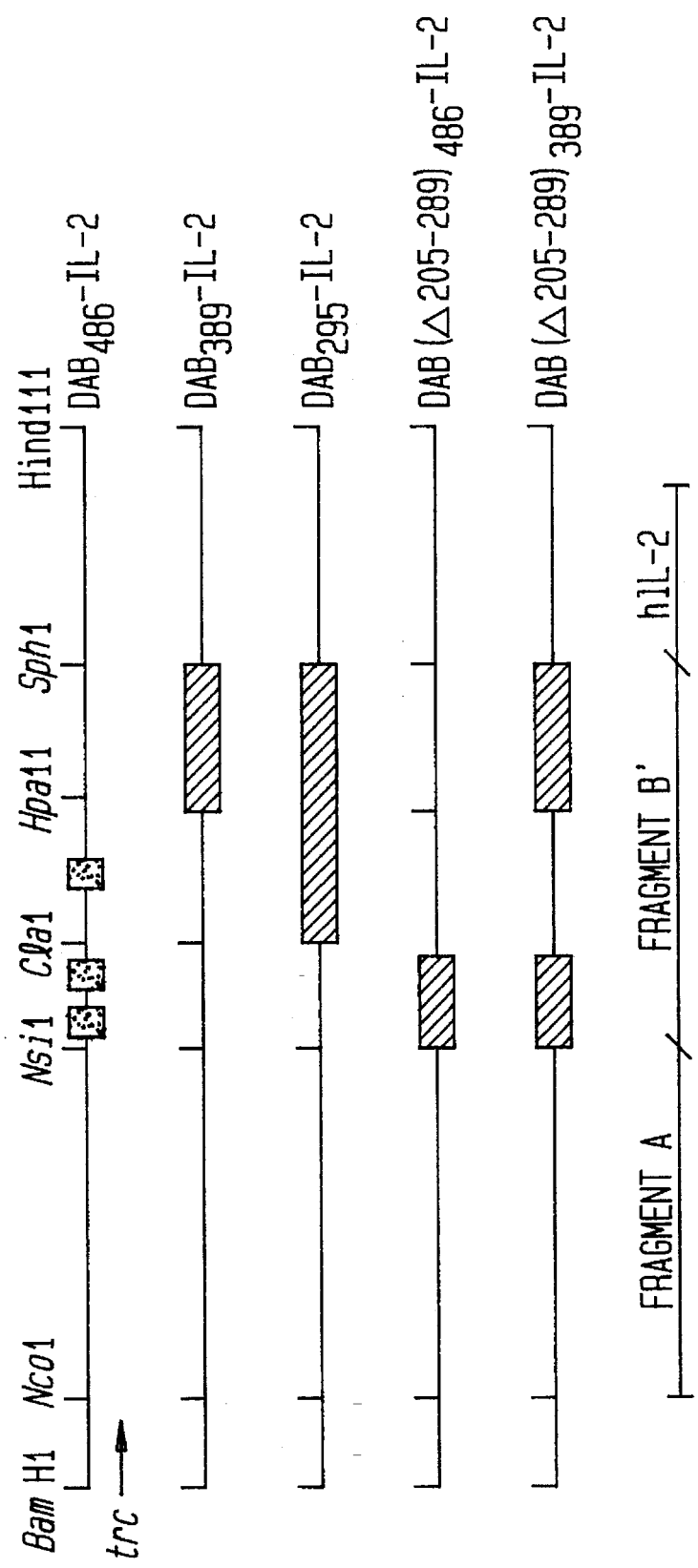
FIG. 3 is a restriction map of DNA sequences encoding various chimeric toxins.

The sequence of DT is given in Greenfield et al. (1983) supra. The sequence encoding IL-2 was synthesized on an Applied Biosystems DNA-Synthesizer, as described in Williams et al. (1988) Nucleic Acids Res. 16:10453–10467, hereby incorporated by reference. The sequence of IL-2 is found in Williams et al. (1988) Nucleic Acids Res. 16:10453–10467. Fusion of the sequence encoding mature DT to ATG using an oligonucleotide linker is described in Bishai et al. (1987) J. Bact. 169:5140–5151, hereby incorporated by reference.

pDW24 is shown in FIG. 2. The insert corresponding to $DAB_{486}$-IL-2 is shown as a heavy line. In FIG. 2 filled circles indicate NcoI sites, open circles indicate NsiI sites, open diamonds indicate ClaI sites, filled squares indicate HpaII sites, open squares indicate SphI sites, and filled triangles indicate SalI sites.

Oligonucleotides and nucleic acids were manipulated as follows. Oligonucleotides were synthesized using cyanoethyl phosphoramidite chemistry on an Applied Biosystems 380A DNA synthesizer (Applied Biosystems Inc., Foster City, Calif.). Following synthesis, oligonucleotides were purified by chromatography on Oligonucleotide Purification Cartridges (Applied Biosystems Inc., Foster City, Calif.) as directed by the manufacturer. Purified oligonucleotides were resuspended in TE buffer (10 mM Tris base, 1 mM EDTA, pH 8.0). To anneal complementary strands, equimolar concentrations of each strand were mixed in the presence of 100 mM NaCl, heated to 90° C. for 10 min, and allowed to cool slowly to room temperature.

Plasmid DNA was purified by the alkaline lysis/cesium chloride gradient method of Ausebel et al. (1989) Current Protocols in Molecular Biology, John Wiley & Sons, N.Y. DNA was digested with restriction endonucleases as recommended by the manufacturer (New England Biolabs, Beverly, Mass. and Bethesda Research Laboratories, Gaithersburg, Md.). Restriction fragments for plasmid construction were extracted from agarose-TBE gels, ligated together (with or without oligonucleotide linkers) and used to transform *E. coli* using standard methods. Ausebel et al (1989) supra and Maniatis et al. (1982), Molecular Cloning Laboratory Manual, Cold Spring Harbor Laboratory, Cold Spring Harbor, N.Y. Plasmid DNA sequencing was performed according to the dideoxy chain termination method of Sanger et al. (1987) Proc. Nat'l Acad. Sci USA 74:5463–5467, as modified by Kraft et al. (1988) Bio Techniques 6:544–547, using Sequenase (United States Biochemicals, Cleveland, Ohio).

Structure of Improved Diphtheria-IL-2 Chimeric Toxins

Expression and purification of chimeric toxins was as follows. All DT-related IL-2 fusion proteins used herein were expressed in the cytoplasm of *E. coli* strain JM101 from the trc promoter, Amann et al. (1985), Gene 40:183–190, hereby incorporated by reference. Recombinant *E. coli* were grown in M9 minimal medium (Maniatis et al. (1982) supra) supplemented with 10 mg/ml casamino acids (Difco, Detroit, Mich.), 50 μg/ml ampicillin, and 0.5 ng/ml thymine in 10 liter volumes in a Microgen Fermentor (New Brunswick Scienctific, Edison, N.J.). Bacterial cultures were grown at 30° C., and sparged with air at 5 L/min. When the absorbance ($A_{590}$nm) of the culture reached 0.3, expression of chimeric tox gene was induced by the addition of isopropyl-β-D- thiogalactopyranoside. Two hours after induction, bacteria were harvested by centrifugation, resuspended in buffer #101 (50 mM $KH_2PO_4$, 10 mM EDTA, 750 mM NaCl, 0.1% Tween 20, pH 8.0), and lysed by sonication (Branson Sonifier). Whole cells and debris were removed by centrifugation at 27,000×g, and the clarified extract was then filter sterilized and applied to an anti-diphtheria toxin immunoaffinity column. Bound proteins were eluted with 4M guanidine hydrochloride, reduced by the addition of β-mercaptoethanol to 1% and then sized by high pressure liquid chromatography on a 7.5×600 mm G4000PW column (TosoHass). Prior to use, fusion toxins were exhaustively dialysed against HEPES buffered Hank's balanced salt solution (Gibco), pH 7.4. Purified diphtheria toxin was purchased from List Biological Laboratories (Campbell, Calif.). For the production of the non-toxic CRM1001, C7(βtox-1001) was grown in 100 ml volumes of C-Y medium (Rappuoli et al. (1983) J. Bact. 153:1201–1210) in 2-liter Erlenmeyer flasks at 35° C. for 20 hrs with shaking (240 rpm). Bacteria were removed by centrifugation at 20,000×g for 15 min. CRM1001 was precipitated from the culture medium by the addition of $NH_4SO_4$ to 70% saturation, and collected by centrifugation. Following dialysis against 10 mM phosphate buffer, pH 7.2, CRM1001 was purified by ion exchange chromatography on DE-52 cellulose as previously described by Pappenheimer et al. (1972), Immunochem. 9:891–906. The concentration of all purified proteins was determined by using Pierce Protein Assay reagent (Pierce Chemical Co., Rockford, Ill.).

$DAB(1001)_{486}$-IL-2 is a chimeric toxin identical to $DAB_{486}$-IL-2 except for the disruption of the disulfide bridge between Cys462 and Cys472 in DAB(1001)$_{486}$-IL-2. DAB(1001)$_{486}$-IL-2 was constructed by replacing the 587 basepair (bp) ClaI-SphI restriction fragment which encodes most of fragment B of DT) of plasmid pDW24 (which carries DAB$_{486}$-IL-2) with the analogous fragment from DNA encoding the TOX-1001 mutant allele of DT. TOX-1001 encodes non-toxic diphtheria toxin-related protein CRM1001 and has been shown to result from a single point mutation which changes Cys471 to Tyr471, Rappuoli et al. (1986) In Protein Carbohydrate Interactions in Biological Systems, Academic Press, Inc., London, pp. 295-296, hereby incorporated by reference. FIG. 3 depicts the restriction maps of DNA encoding DAB$_{486}$-IL-2 and the corresponding fusion protein encoded by DAB$_{486}$-IL-2. (In FIG. 3 stippled boxes between the NsiI and HpaII restriction endonuclease sites designate the diphtheria toxin fragment B-related sequences which encode the membrane associating domains. The amphipathic domain is encoded between the NsiI and ClaI sites, and the putative membrane spanning domains are encoded between the ClaI and HpaII sites. Hatched boxes indicate the relative position of internal in-frame deletion mutations.) The construction of pDW26, which encodes the chimeric toxin with the Cys 472 to Tyr 472 mutation, is shown in FIG. 2. Following ligation and transformation, the DNA sequence of the tox-1001 portion of the gene fusion DAB (1001)$_{486}$-IL-2 was determined in order to insure that the Cys471 to Tyr471 mutation was recloned. E. coli (pDW26), was grown in M9 minimal media, cells were harvested, lysed and the fusion toxin, designated DAB(1001)$_{486}$-IL-2, was purified by immunoaffinity chromatography and HPLC.

The dose response capacity of DAB$_{486}$-IL-2, CRM1001, and DAB(1001)$_{486}$-IL-2 to block [$^{14}$C]-leucine incorporation by high affinity IL-2 receptor bearing HUT 102/6TG cells was determined. As anticipated, DAB$_{486}$-IL-2 was highly toxic for these cells (IC$_{50}$=4×10$^{-10}$M); whereas, CRM1001 was found to be non-toxic. In marked contrast to CRM1001, however, the fusion toxin which carries the Cys472 to Tyr472 mutation, DAB(1001)$_{486}$-IL-2, was found to be as toxic for HUT 102/6TG cells as the wild type DAB$_{486}$-IL-2. These results demonstrate that the fragment B disulfide bond is not required for biological activity of the fusion toxin.

HUT 102/6TG cytotoxicity assays were performed as follows. Cultured HUT 102/6TG cells were maintained in RPMI 1640 medium (Gibco, Grand Island, N.Y.) supplemented with 10% fetal bovine serum (Cellect, GIBCO), 2 mM glutamine, and penicillin and streptomycin to 50 IU and 50 µg/ml, respectively. For cytotoxicity assays, cells were seeded in 96-well V-bottomed plates (Linbro-Flow Laboratories, McLean, Va.) at a concentration of 5×10$^4$ per well in complete medium. Toxins, or toxin-related materials, were added to varying concentrations (10$^{-12}$M to 10$^{-6}$M) and the cultures were incubated for 18 hrs at 37° C. in a 5% CO$_2$ atmosphere. Following incubation, the plates were centrifuged for 5 min. at 170×g and the medium removed and replaced with 200 µl leucine-free medium (MEM, Gibco) containing 1.0 µCi/ml [$^{14}$C]-leucine (New England Nuclear, Boston, Mass.). After an additional 90 min. at 37° C., the plates were centrifuged for 5 min. at 170×g, the medium was removed and the cells were lysed by the addition of 4M KOH. Protein was precipitated by the addition of 10% trichloroacetic acid and the insoluble material was then collected on glass fiber filters using a cell harvester (Skatron, Sterling, Va.). Filters were washed, dried, and counted according to standard methods. Cells cultured with medium alone served as the control. All assays were performed in quadruplicate.

Since the disulfide bond between Cys462–Cys472 was not required for the cytotoxic action of DAB$_{486}$-IL-2, it was of interest to determine what DT fragment B sequences were essential for the delivery of fragment A to the cytosol. Several in-frame deletion mutations were introduced into the fragment B encoding portion of the DAB$_{486}$-IL-2 toxin gene, FIGS. 1b, 2, and 3. FIG. 1b shows the structure of DAB$_{486}$-IL-2 and various mutants derived from DAB$_{486}$-IL-2. In FIG. 1b a wide bar indicates the fusion protein, narrow connecting lines represent deletions, numbers above the bars are amino acid residue numbers in the DAB nomenclature, numbers below the bars correspond to the amino acid residue numbering of native DT, cross hatching indicated amphipathic regions, darkened areas correspond to the transmembrane region, IL-2-2-133 indicates amino acid residues 2-133 of IL-2, Ala=alanine, Asn=asparagine, Asp=aspartic acid, Cys=cysteine, Gly=glycine, His=histidine, Ile=isoleucine, Met=methionine, Thr=threonine, Tyr=tyrosine, and Val=valine.

The first mutant, DAB$_{389}$-IL-2 was constructed by removing a 309 bp HpaII—SphI restriction fragment from pDW24 and replacing it with oligonucleotide linker 261/274 (Table 1) to generate plasmid pDW27 (FIG. 1). This linker restores fragment B sequences from Pro383 to Thr387, and allows for in-frame fusion to IL-2 sequences at this position. Thus, in DAB$_{389}$-IL-2 the 97 amino acids between Thr387 and His485 have been deleted.

TABLE 1

| | Oligonucleotide linkers. | |
|---|---|---|
| construct | oligonucleotide identification number | linker |
| DAB$_{389}$-IL-2 | 274 | 5'-CG GGT CAC AAA ACG CAT G-3' |
| | 261 | CCA GTG TTT TGC |
| | | ½HpaII    ½SphI |
| DAB$_{295}$-IL-2 | 292 | 5'-C GAT GGT GTG CAT G-3' |
| | 293 | TA CCA CAC |
| | | ½ClaI    ½SphI |
| DAB(Δ205–289)$_{486}$-IL-2 | 337 | 5'-TA AAT AT-3' |
| | 338 | ACG TAT TTA TAG C |
| | | ½NsiI    ½ClaI |
| DAB(Δ205–289)$_{389}$-IL2 | 337 | 5'-TA AAT AT-3' |
| | 338 | ACG TAT TTA TAG C |
| | | ½NsiI    ½ClaI |

In a similar fashion, a 191 amino acid in-frame deletion was constructed by removing a ClaI—SphI restriction fragment from pDW24 and replacing it with the 292/293 oligonucleotide linker (Table 1) to form plasmid pDW28 which encodes $DAB_{295}$-IL-2. In this case, the in-frame deletion encompasses the putative membrane-spanning helices that have been predicted by Lambotte et al. (1980) J. Cell. Biol. 87:837–840, to play a role in the delivery of fragment A to the eukaryotic cell cytosol.

Figure 4:
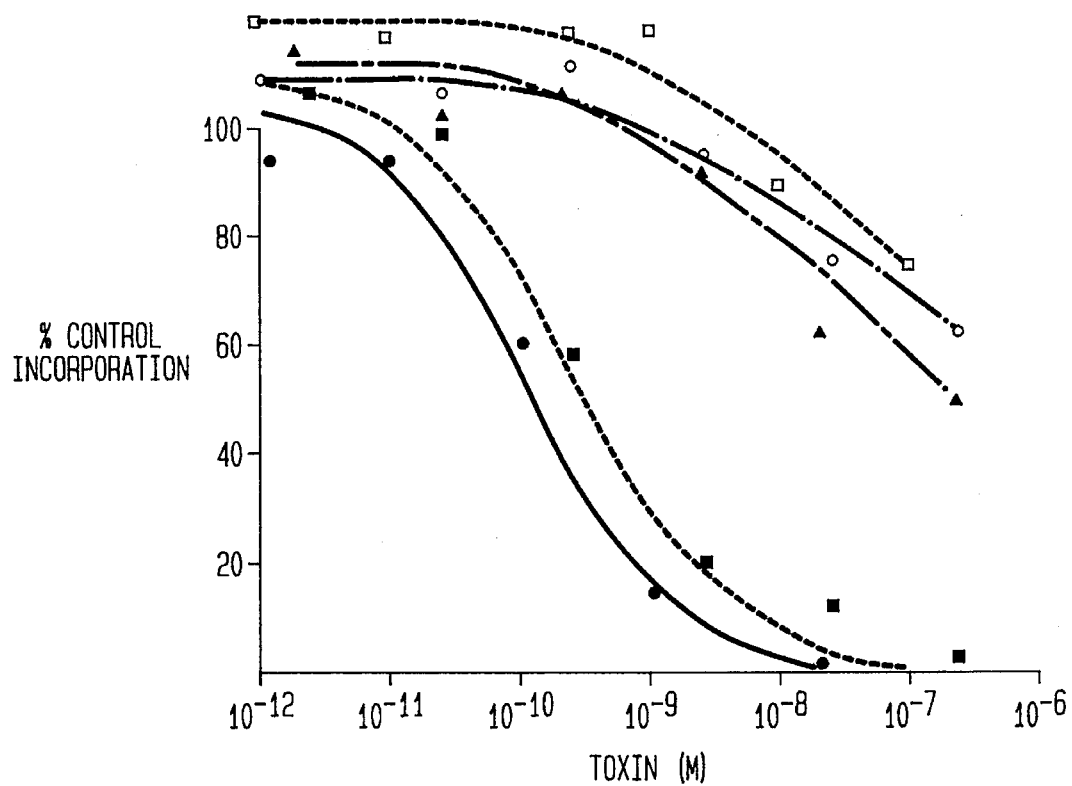
FIG. 4 is a graph of the effects of varying doses of chimeric toxins on cultured cells.

Purified, $DAB_{389}$-IL-2 and $DAB_{295}$-IL-2 were found to have electrophoretic mobilities of 57 kDa and 47 kDa, respectively. The dose response analysis on HUT 102/6TG cells is shown in FIG. 4. In FIG. 4 $DAB_{486}$-IL-2 is indicated by filled squares; $DAB_{389}$-IL-2 is indicated by filled circles; $DAB_{295}$-IL2 is indicated by open circles; $DAB(\Delta 205-289)_{486}$-IL-2 (see below) is indicated by open squares; and $DAB(\Delta 205-289)_{389}$-IL-2 (see below) is indicated by open triangles. $DAB_{486}$-IL-2 and $DAB_{389}$-IL-2 exhibited an $IC_{50}$ of approximately $4 \times 10^{-10}$M and $1 \times 10^{-10}$M, respectively. In marked contrast, the $IC_{50}$ of $DAB_{295}$-IL-2 was approximately 1,000-fold lower ($4 \times 10^{-7}$M). These results suggest that fragment B sequences between Thr 387 and His 486 do not play a major role in the delivery of fragment A to the cytosol. Sequences between Ser292 and Thr387 on the other hand are essential for the efficient delivery of fragment A.

Surprisingly, $DAB_{389}$-IL-2 possessed much greater activity than did $DAB_{486}$-IL-2. $DAB_{389}$-IL-2, which lacks native DT residues 387 through 483, and which has increased toxic activity, leaves the hydrophobic transmembrane segment located approximately between native DT residues 346 and 371 intact. See Lambotte et al. (1980) J. Cell Biol. 87:837–840, hereby incorporated by reference, for a characterization of the transmembrane region. $DAB_{295}$-IL-2, which removes native DT residues 291 through 481, and which has greatly reduced toxicity, removes the transmembrane region (346–371).

Figure 5:
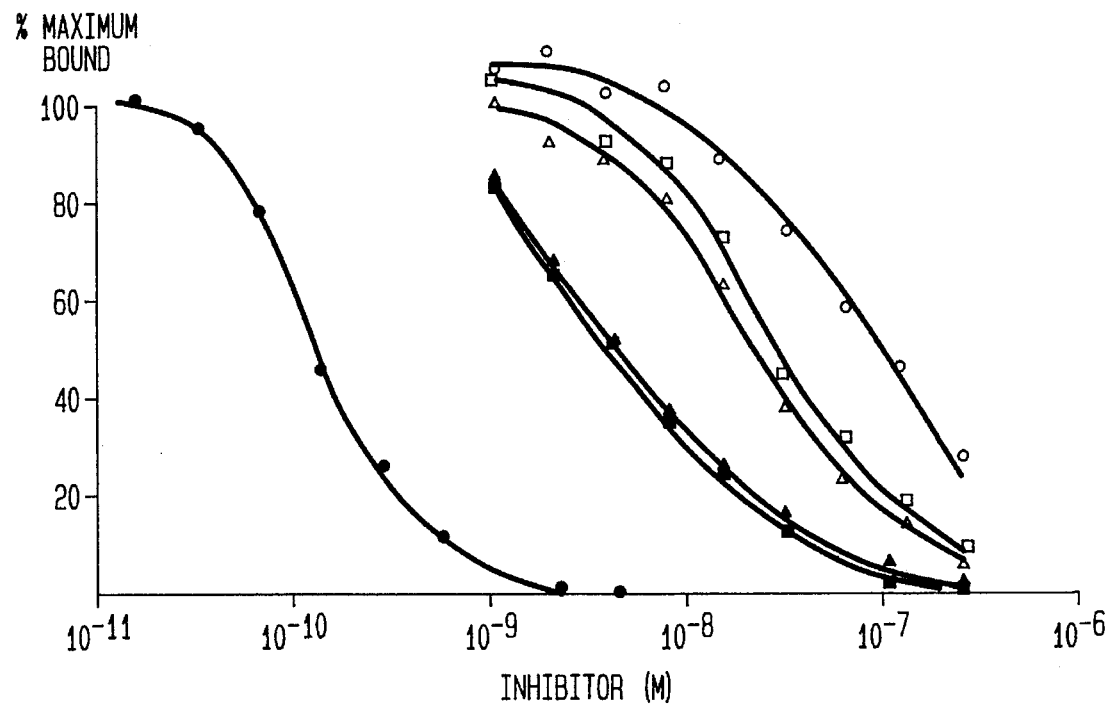
FIG. 5 is a graph of the ability of chimeric toxins to competitively displace [$^{125}$I]-labeled IL-2 from the high affinity IL-2 receptor.

In order to rule out the possibility that the reason for the low potency of $DAB_{295}$-IL-2 for HUT 102/6TG cells was related to altered binding to the high affinity IL-2 receptor, we have conducted a series of competitive displacement experiments using $[^{125}I]$-rIL-2. FIG. 5 shows the competitive displacement of $[^{125}I]$-labeled IL-2 from the high affinity IL-2 receptor by unlabeled rIL-2 depicted by filled circles; $DAB_{486}$-IL-2 depicted by open triangles; $DAB_{389}$-IL-2 depicted by closed squares; $DAB_{295}$-IL-2 depicted by closed triangles; $DAB(\Delta 205-289)_{486}$-IL-2 (see below) depicted by open circles; and $DAB(\Delta 205-289)_{389}$-IL-2 (see below) depicted by open squares. The concentration of $[^{125}I]$-IL-2 used was 10 pM and the specific activity was approximately 0.7 µCi/pmol. As shown in Table 2, both $DAB_{389}$-IL-2 and $DAB_{295}$-IL-2 were found to have an apparent $K_d$ that is approximately 3-times lower than that of $DAB_{486}$-IL-2 ($K_d=8\times 10^{-9}$M vs. $K_d=2.5\times 10^{-8}$M). It is particularly significant that competitive displacement experiments showed that both $DAB_{389}$-IL-2 and $DAB_{295}$-IL-2 bind more avidly to the high affinity IL-2 receptor than does $DAB_{486}$-IL-2(Kd=$8\times 10^{-9}$ and $8.4\times 10^{-9}$M vs. Kd=$2.5\times 10^{-8}$M). These results provide evidence that fusion of IL-2 sequences to toxophores of smaller mass may serve to position the IL-2 binding domain for more favorable receptor interaction.

It is of interest to note that while $DAB_{295}$-IL-2 binds more avidly to the high affinity IL-2 receptor than $DAB_{486}$-IL-2, its cytotoxic activity is at least 1,000-fold lower (FIG. 4). These results indicated that avid binding to the target receptor is not in itself sufficient for the biologic activity of the DT-related IL-2 fusion toxins, and that fragment B sequences between Ser292 and Thr387 are essential for a post-receptor binding event in the intoxication process.

TABLE 2

Relative ability of rIL-2 and DAB-IL-2 related fusion proteins to displace $[^{125}I]$--rIL-2 from high affinity IL-2 receptors on HUT 102/6TG cells

| unlabeled ligand | apparent $K_d$ | $K_d$ DAB-IL-2/rIL-2 |
| --- | --- | --- |
| rIL-2 | $1.7 \times 10^{-10}$ | — |
| $DAB_{486}$-IL-2 | $2.5 \times 10^{-8}$ | 147 |
| $DAB_{389}$-IL-2 | $8.0 \times 10^{-9}$ | 47 |
| $DAB_{295}$-IL-2 | $8.4 \times 10^{-9}$ | 49 |
| $DAB(\Delta 205-289)_{486}$-IL-2 | $1.0 \times 10^{-7}$ | 588 |
| $DAB(\Delta 205-289)_{389}$-IL-2 | $2.9 \times 10^{-8}$ | 170 |

Competitive displacement of $[^{125}I]$-rIL-2 by rIL-2 and DAB-IL-2 fusion toxins was determined as follows. The radiolabeled IL-2 binding assay was performed essentially as described by Wang et al. (1987) J. Exp. Med. 166:1055–1069. Cells were harvested and washed with cell culture medium. HUT 102/6TG cells were resuspended to $5\times 10^6$ per ml and incubated with $[^{125}I]$-rIL-2 (0.7 µCi/pmol) in the presence or absence of increasing concentrations of unlabeled rIL-2 or the DAB-IL-2 fusion toxins for 30 min. at 37° C. under 5% $CO_2$. The reaction was then overlayed on a mixture of 80% 550 fluid (Accumetric Inc., Elizabethtown, Ky.) : 20% parafin oil (d=1.03 g/ml) and microcentrifuged. The aqueous phase and the pellet of each sample, representing free and bound ligand, respectively, was then counted in a Nuclear Chicago gamma counter. Apparent dissociation constants, $K_d$, were determined from the concentrations of unlabeled ligand required to displace 50% of radiolabeled rIL-2 binding to receptors.

In order to test the hypothesis that an amphipathic region (amino acids 210–252 in $DAB_{486}$-IL-2) plays a role in the intoxication process, in-frame deletions of the 85 amino acid encoding region from NsiI to ClaI of both pDW24 and pDW27 to form pDW30 (containing $DAB(\Delta 205-289)_{486}$-IL-2) and pDW31 (containing $DAB(\Delta 205-289)_{389}$-IL-2), respectively (FIGS. 2 and 3; Table 1) were constructed. Following ligation and transformation, the DAB-IL-2 related fusion proteins were expressed and purified, as described above. As shown in FIG. 4, the deletion of fragment B sequences which include the amphipathic region result in a marked loss of cytotoxic activity against high affinity IL-2 receptor positive cells in vitro. It is of interest to note that DAB ($\Delta 205-289)_{389}$-IL-2 was found to displace radiolabeled IL-2 from the high affinity receptor almost as well as $DAB_{486}$-IL-2; whereas, $DAB(\Delta 205-289)_{486}$-IL-2 was found to bind 4-fold less avidly to the receptor (FIG. 5).

Increased Resistance to Proteolytic Degradation

The chimeric toxin encoded by $DAB_{389}$-IL-2 is more resistant to proteolytic degradation than is the chimeric toxin encoded by $DAB_{486}$-IL-2. When purified, as described above, and analysed on SDS-polyacrylamide gels, the $DAB_{389}$-IL-2 hybrid toxin is accompanied by very few degradation products (as evidenced by the relative absence of bands of smaller size than that of the intact chimeric toxin). Purified $DAB_{486}$-IL-2 on the other hand is accompanied by numerous dark bands of lower molecular weight than the intact chimeric toxin. These lower molecular weight bands react with anti-$DAB_{486}$-IL-2 antibodies, supporting the conclusion that they are degradation products.

Sodium dodecylsulfate (SDS)-polyacrylamide gel electrophoresis (PAGE) was performed according to the method of Laemmli (1970) Nature 227:680–685 using 12% gels and a Mini-Protein II gel apparatus (BioRad). Proteins were fixed in 12.5% trichloroacetic acid for 5 min and stained with Coomassie brilliant blue according to the Diezal procedure, Diezal et al. (1972) Anal. Blochem. 48:617–624.

Construction of Fusion Genes Encoding DT-EGF Chimeric Toxins $DAB_{486}EGF$ and $DAB_{389}$ EGF can be constructed in a manner analogous to that in which $DAB_{486}$-IL-2 and $DAB_{389}$-IL-2 were constructed, by methods known to those skilled in the art. To construct a plasmid encoding $DAB_{486}$ fused to EGF, plasmid pDW24 (which encodes $DAB_{486}$ fused to IL-2) is digested with SphI and HindIII to remove the IL-2 coding sequence. The resulting pDW24 SphI-HindIII fragment containing the sequence encoding DT residues 1–485 is ligated to a synthetic SphI-HindIII fragment encoding EGF to yield a plasmid encoding $DAB_{486}$ fused to EGF. The EGF fragment, shown in FIG. 6, was synthesized, as described, using preferred codons for expression in E. coli (see Grosjean et al. (1982) Gene 18:199–209, hearby incorporated by reference). The synthetic fragment includes appropriate linkers at the 5' and 3' ends for insertion into the plasmid and for in-frame fusion to the DT coding sequence.

To construct a plasmid encoding $DAB_{389}$ fused To EGF a similar protocol can be followed, except that pDW27 (which encodes $DAB_{389}$ fused to IL-2) is used in place of pDW24. The IL-2 encoding DNA is removed from pDW27 by digestion with SphI and HindIIi and EGF encoding DNA is inserted in its place, resulting in a $DAB_{389}$ fused in frame to EGF. The same synthetic EGF fragment used in the construction of the $DAB_{489}EGF$ fusion (FIG. 6) can be used.

Those skilled in the art will realize that the protocols given above are not the only way of making the chimeric toxins of the invention. Refinements include changes in pDW24, pDW27, and plasmids derived therefrom directed toward compliance with the Good Manufacturing Practises of the Food and Drug Administration, e.g., the inclusion of the $lacI^q$ gene (Amersham) and the replacement of the ampicillin resistance gene ($amp^r$) with the gene for neomycin/kanamycin resistance from Tn5 (Pharmacia) in the plasmids that are used for expression of the chimeric toxins of the invention. These alterations can be performed without undue experimentation by one skilled in the art.

Figure 7A:
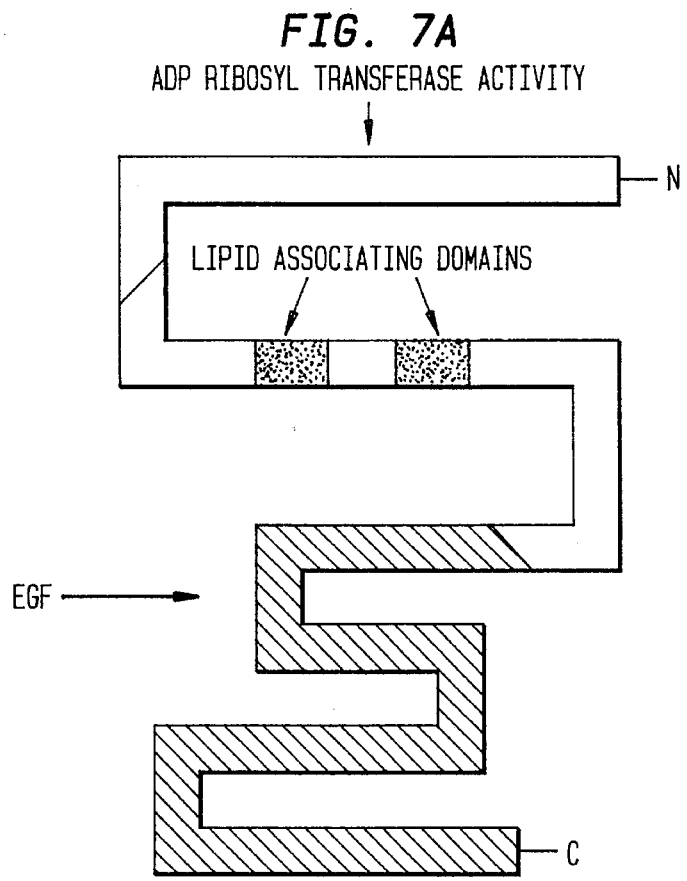
FIG. 7 is a diagramatic representation of $DAB_{486}$EGF and $DAB_{389}$EGF.
Figure 7B:
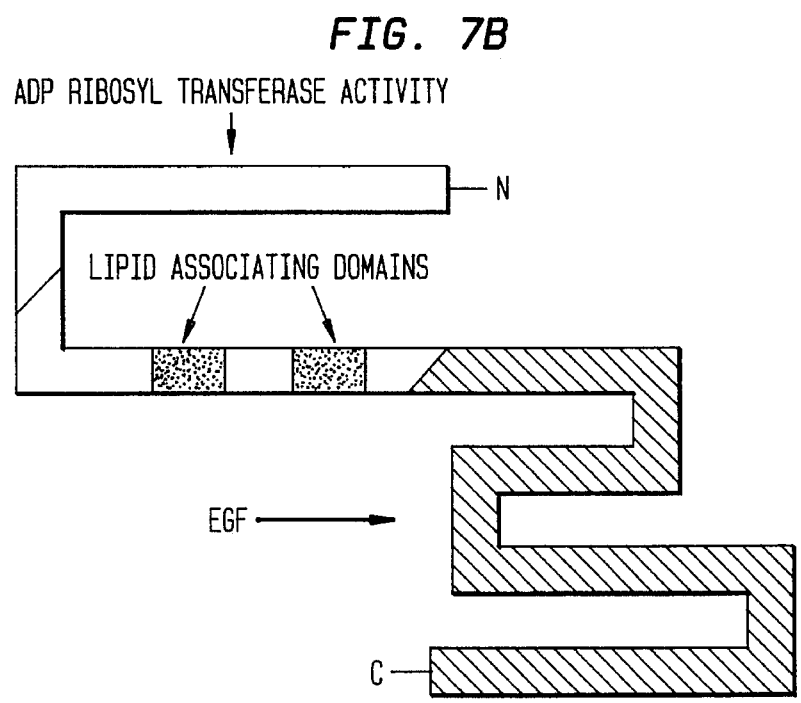

The Biological Activity of DT-EGF Chimeric Toxins $DAB_{486}EGF$ and $DAB_{389}EGF$ are the products of fusion genes in which the receptor binding domain of DT has been removed and replaced with DNA encoding human EGF. As shown in FIG. 7, the resulting proteins contain the enzymatically active fragment A of DT and the lipid associating domains of fragment B of DT required for translocation of fragment A into the cytosol. $DAB_{389}EGF$ differs from $DAB_{486}EGF$ by the deletion of the 97 amino acids immediately 5' to amino acid residue 484 of DT. The EGF portion of both $DAB_{486}EGF$ and $DAB_{389}EGF$ governs receptor binding. Thus, these molecules have the potential to specifically target the cytotoxicity of DT to tumor cells characterized by EGF receptor expression.

DT-EGF Chimeric Toxins Are Toxic to EGF-Receptor-Bearing Cells. The cytotoxicity of $DAB_{486}EGF$ for a panel of human cell lines was assessed and compared to A431 cells (ATCC CRL 1555), a human epidermoid carcinoma cell line with a high number of EGF receptors. The results are shown in Table 3. Included in the study were human tumor cell lines which have been reported to express high numbers of EGF receptors (e.g., BT-20, HeLa, LNCaP and U-87 MG) as well as human tumor cell lines (e.g., C91/PL, BeWo and A375) and normal tissue cell lines (e.g., WI-38, Hs 67 and HEPM) expressing few or no EGF receptors. Cytotoxicity was evaluated as follows. Cells were plated in triplicate wells of 96 well plates with $DAB_{486}EGF$ in assay medium appropriate to the cell type (see Table 3). $DAB_{486}EGF$ concentrations were between $10^{-15}$ and $10^{-7}M$. Following a 20-hour incubation, cells were labeled with [$^{14}C$]leucine, trypsinized, harvested onto glass fiber filter mats and counted to determine the percent of control incorporation. Cell lines exhibiting an $IC_{50}$ for $DAB_{486}EGF$ of less than 0.5 nM were considered sensitive.

TABLE 3

The effect of a DT-EGF chimeric toxin on various cell lines

Tumor Cell lines

| Cell Line | Tissue/Type | Sensitivity |
| --- | --- | --- |
| A431 | vulval epidermoid carcinoma | + |
| A549 | lung carcinoma | + |
| KB | oral epidermoid carcinoma | + |
| BT-20 | breast adenocarcinoma | + |
| HeLa S3 | cervical carcinoma | + |
| T47D | breast ductal carcinoma | + |
| LNCaP.FG | prostate carcinoma | + |
| HOS | osteosarcoma | + |
| U-87 MG | glioblastoma/astrocytoma | + |
| C91/PL | HTLV-1 transformed T cell | − |
| BeWo | choriocarcinoma | − |
| A375 | malignant melanoma | − |
| MCF-7 | breast adenocarcinoma | − |
| SNU-C2B | cecum carcinoma | − |

Normal Cell Lines

| Cell Line | Tissue | Sensitivity |
| --- | --- | --- |
| WI-38 | diploid lung fibroblast | − |
| Hs 67 | thymus | − |
| CCD-18Co | colon fibroblast | − |
| HISM | smooth muscle, jejunum | − |
| FH74s Int | fetal small intestine | − |
| HEPM | embryonic palatal mesenchyme | − |

Growth conditions and passage schedules used were those defined by ATCC (except as noted below). Culture media were as follows: A431 (ATCC CRL1555), DMEM+10% FCS; A549 (ATCC CCL185) Ham's F12+10% FCS; KB (ATCC CCL17), DMEM+NEAA+10% FCS; BT-20 (ATCC HTB19), MEM+10% FCS; HeLa S3 (ATCC CCL2.2), Ham's F12 +10% FCS; T47D (ATCC HTB133), RPMI 1640+10% FCS; LNCaP.FG (ATCC CRL1740), RPMI 1640+10% FCS; HOS (ATCC CRL1543), MEM+10% FCS; U-87 MG (ATCC HTB14), MEM+10% FCS; C91/PL (from Robert Swartz, NEMC, Boston, Mass., see Bacha et al. (1988) J. Exp. Med. 167:612 for growth conditions), RPM1 1640+15% FCS; BeWo (ATTC CCL98), Ham's F12+15% FCS; A375 (ATCC CRL 1619), DMEM+10% FCS; MCF-7 (ATCC TB22) MEM+10% FCS; SNU-C2B (ATCC CCL250) RPM1 1640+10% FCS; WI-38 (ATCC CCL75), Eagle's Basal+10% FCS; Hs 67 (ATCC HTB 163), DMEM+ 10% FCS; CCD-18Co (ATCC CRL 1459), MEM+10% FCS; HISM (ATCC CRL 1692), DMEM+10% FCS; FHs74Int (ATCC CCL241), DMEM+10% FCS; HEPM (ATCC CRL 1486), MEM+10% FCS. DMEM=Dulbecco's modified Eagles Medium; MEM=Minimum Essential Medium; NEAA=Non-Essential Amino Acids; FCS=Fetal Calf Serum; ATCC=American Type Culture Collection.

Figure 8:
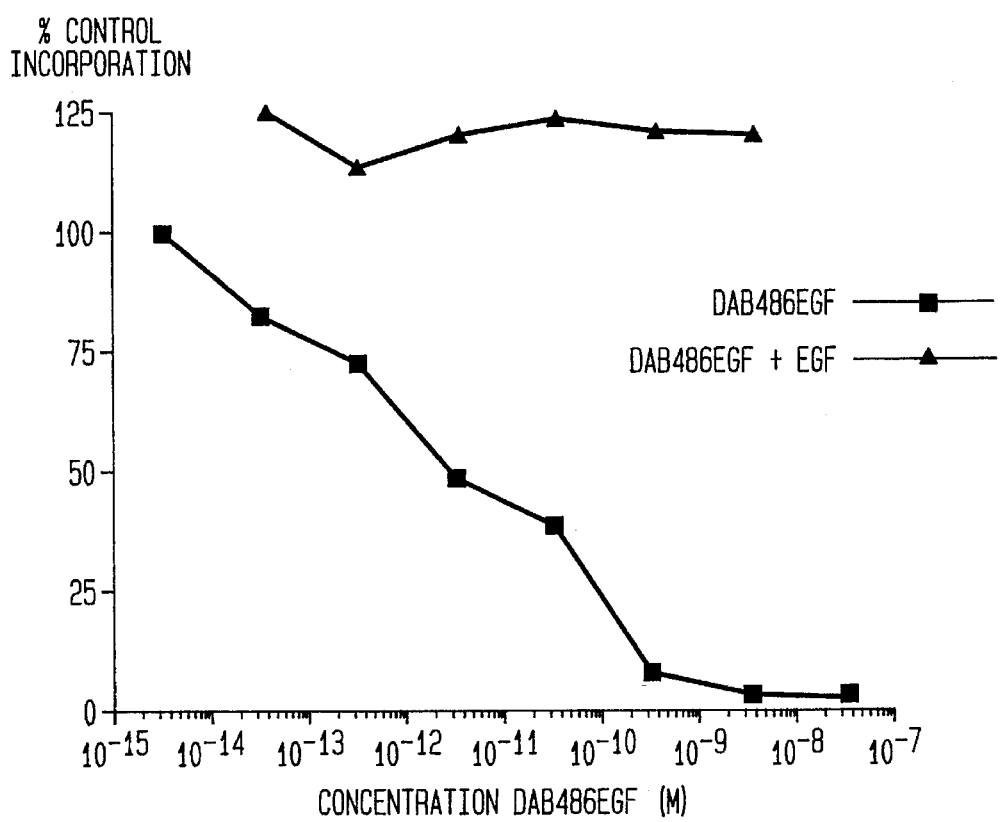
FIG. 8 is a graph showing the effect of EGF on $DAB_{486}$EGF cytotoxicity.
Figure 9:
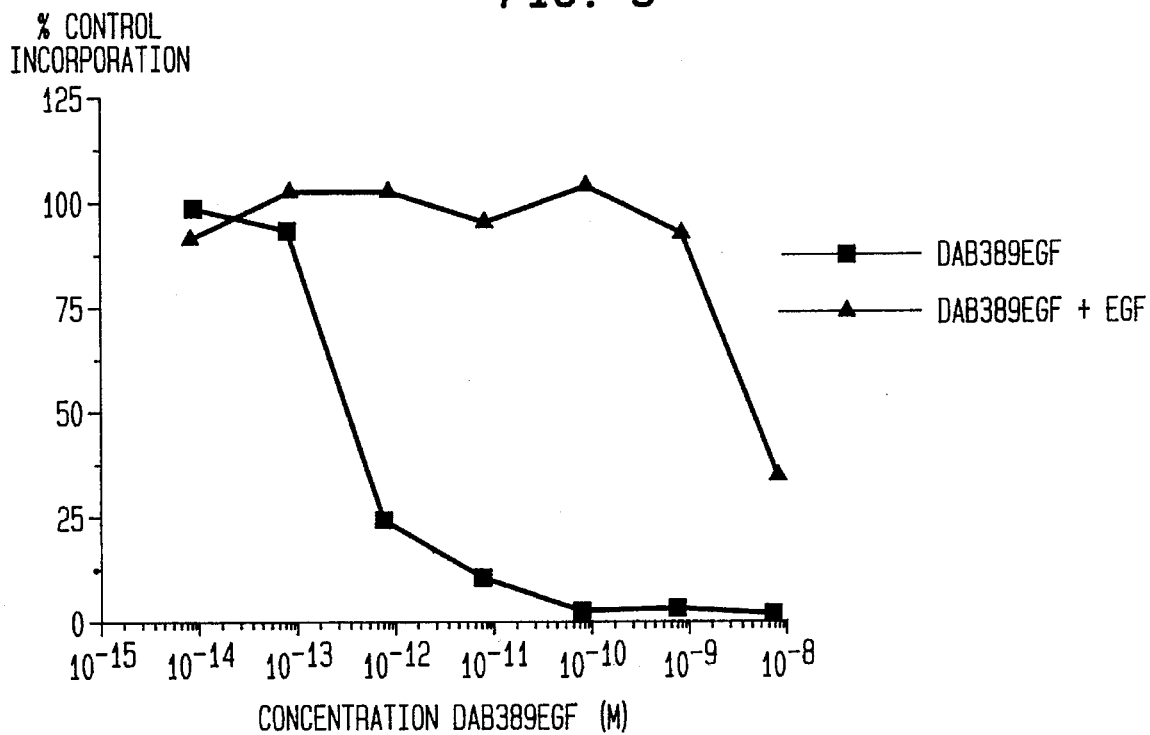
FIG. 9 is a graph showing the effect of EGF on $DAB_{389}$EGF cytotoxicity.

To demonstrate that the cytotoxic action of $DAB_{486}EGF$ and $DAB_{389}EGF$ are mediated selectively by the EGF receptor, A431 cells were plated in triplicate wells of 96 well plates with $DAB_{486}EGF$ (FIG. 8) or $DAB_{389}EGF$ (FIG. 9) in the presence of the specific competitor of the EGF receptor, human EGF (Upstate Biotechnologies, Inc.) ($10^{-7}M$), in assay medium (DMEM +10% FCS). In FIG. 8 solid squares indicate $DAB_{486}$ EGF and solid triangles indicate $DAB_{486}EGF+EGF$. In FIG. 9 solid squares indicate $DAB_{389}EGF$ and solid triangles indicate $DAB_{389}EGF+EGF$. Following a 20-hour incubation at 37° C., cells were labeled with [$^{14}C$]leucine, trypsinized, harvested onto glass fiber filter mats and counted to determine the percent of control incorporation. The results show that, in the absence of EGF, $DAB_{486}EGF$ and $DAB_{389}EGF$ inhibit protein synthesis with an $IC_{50}$ of $3\times10^{-12}M$ and $3\times10^{-13}M$, respectively. EGF almost completely abolishes this activity. Likewise, anti-EGF (Biomedical Technologies, Inc.) and anti-EGF receptor (Upstate Biotechnologies, Inc.) also abolish the cytotoxicity of $DAB_{486}EGF$ and $DAB_{389}EGF$ while the nonspecific competitors, transferrin (Sigma) anti-transferrin (Dako), and anti-transferrin receptor (Dako), have no effect. These results demonstrate that $DAB_{486}EGF$ and $DAB_{389}EGF$ are potent and specific cytotoxic agents. Note that $DAB_{389}EGF$ is approximately 10 times more potent than $DAB_{486}EGF$.

Figure 10:
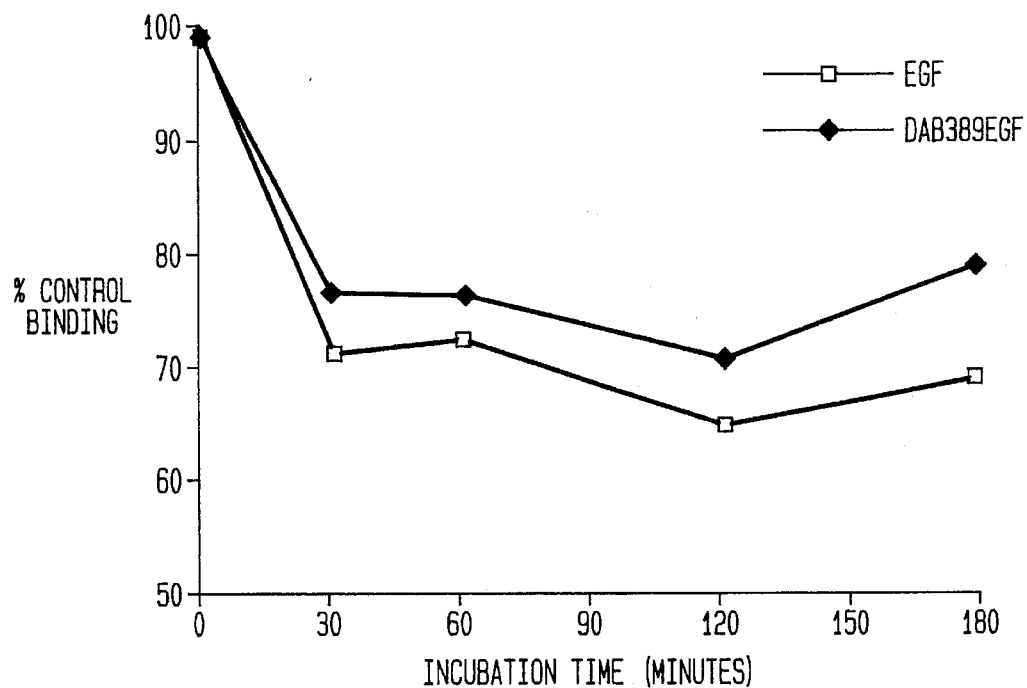
FIG. 10 is a graph showing the effect of EGF and $DAB_{389}$EGF on the EGF binding capacity of A431 cells.

$DAB_{389}EGF$, like EGF, induces down regulation of the EGF receptor, providing further evidence for the EGF receptor-specific nature of DT-EGF chimeric toxins. Binding and internalization of EGF induces down regulation of the EGF receptor which can be detected as a decrease in [$^{125}I$]EGF binding capacity (Krupp et al. (1982) J. Biol. Chem. 257:11489). The ability of $DAB_{389}EGF$ to induce EGF receptor internalization and subsequent down regulation was evaluated and compared to that induced by native EGF. The results are shown in FIG. 10. In FIG. 10 open squares indicate EGF and closed diamonds indicate $DAB_{389}EGF$. A431 cells in triplicate wells of 24 well plates were preincubated with EGF or $DAB_{389}EGF$ ($10^{-8}M$) for the indicated times in DMEM+0.1% BSA (bovine serum albumin) at 37° C. The cells were then placed on ice and acid stripped (with 0.2M acetic acid, 0.5M NaCl) to remove bound, but not internalized, EGF or $DAB_{389}EGF$. EGF binding capacity was measured by incubating the cells, on ice, with [$^{125}I$]EGF. Following a 90-minute incubation the cells were washed, solubilized, and counted.

Figure 11:
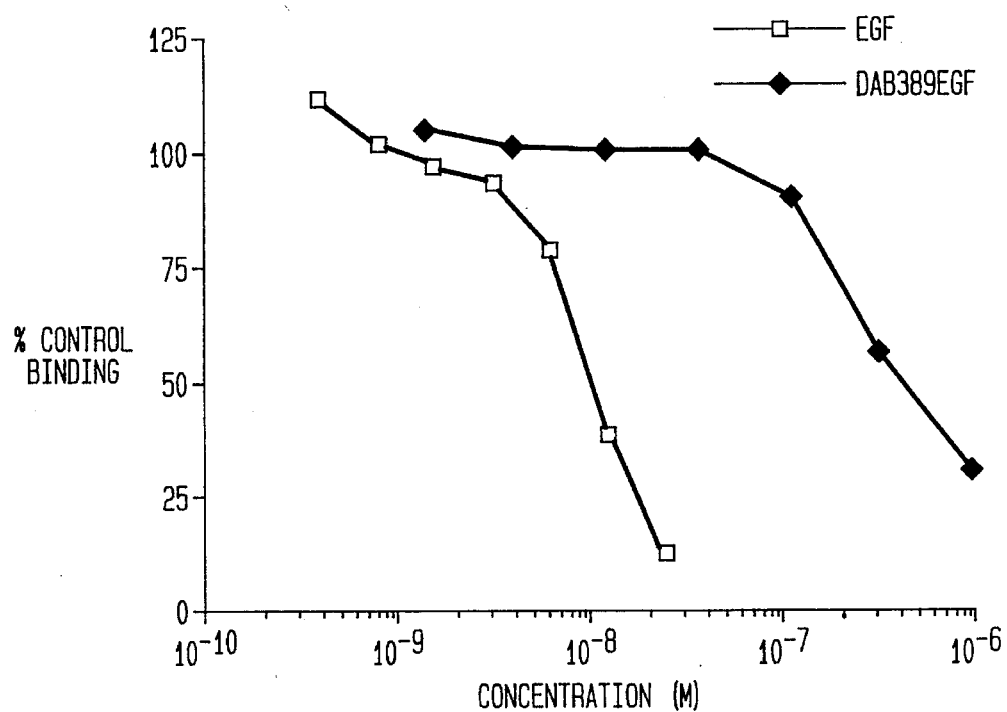
FIG. 11 is a graph showing the ability of EGF or $DAB_{389}$EGF to displace [$^{125}$I] EGF from EGF receptors.

An EGF receptor-dependent interaction is also shown by the fact that $DAB_{389}EGF$, like EGF, displaces [$^{125}I$]EGF from the EGF receptor, as shown in FIG. 11. In FIG. 11 open squares indicate EGF and solid diamonds indicate $DAB_{389}EGF$. Results in FIG. 11 are expressed as a percent of control (no competition) cpm. The ability of $DAB_{389}EGF$ to displace high affinity [$^{125}I$]EGF binding to A431 cells was evaluated as follows. A431 cells, plated in triplicate wells of 24 well plates, were preincubated in binding media (phosphate buffered saline pH 7.2+0.1% BSA+15 mM sodium azide+50 mM 2-deoxyglucose) for 1 hour at 37° C. and then incubated with [$^{125}I$]EGF in binding media in the presence of $DAB_{389}EGF$ or EGF. Following incubation, the cells were washed, solubilized and counted. The results are summarized in Table 4.

In Table 4 $EC_{50}$ is the concentration resulting in displacement of 50% of the [$^{125}I$] EGF.

TABLE 4

Displacement of [$^{125}I$] EGF Binding by EGF and $DAB_{389}EGF$

| Competition | $EC_{50}$ | fold over [$^{125}I$]EGF | fold over EGF |
|---|---|---|---|
| EGF | $1.0 \times 10^{-8}$ M | 20 | — |
| $DAB_{389}EGF$ | $4.5 \times 10^{-7}$ M | 900 | 45 |

Cytotoxicity of DT-EGF Chimeric Toxins is DT Dependent. Upon binding to its receptor, the cellular uptake of native DT occurs by endocytosis of clathrin coated vesicles (Middlebrook et al. (1978) J. Biol. Chem. 253:7325). DT is then found in endosomes where the low pH induces a conformational change facilitating the translocation of the enzymatic fragment A portion of DT into the cytosol. To determine if the cytotoxicity of $DAB_{486}EGF$ and $DAB_{389}EGF$ is also dependent upon the same pathway, A431 cells were plated in sextuplicate wells of 96 well plates containing $DAB_{486}EGF$, $DAB_{389}EGF$ or DMEM+10% FCS in the absence or presence of chloroquine ($10^{-5}M$) (Sigma). Chloroquine is a lysosomotropic compound which prevents acidification of endosomes (Kim et al. (1965) J. Bacteriol. 90:1552). Following a 20-hour incubation at 37° C., the cells were labeled with [$^3H$]leucine, trypsinized, harvested onto glass fiber filter mats and counted. The results are shown in Table 5, expressed as the percent of control (no $DAB_{486}EGF$ or $DAB_{389}EGF$) incorporation and represent the mean of three experiments. The results show that chloroquine blocks the cytotoxicity of DT-EGF chimeric toxins.

TABLE 5

Sensitivity of DAB-EGF Chimeric Toxin-Cytotoxicity to Chloroquine

| | Percent of Control Incorporation | |
|---|---|---|
| | No Addition | Chloroquine |
| $DAB_{486}EGF$ Concentration | | |
| 0 | 100 | 86 |
| $10^{-8}$ M | 5 | 60 |
| $10^{-9}$ M | 25 | 96 |
| $DAB_{389}EGF$ Concentration | | |
| 0 | 100 | 73 |
| $10^{-11}$ M | 4 | 61 |
| $10^{-12}$ M | 57 | 100 |

Following translocation into the cytosol, fragment A catalyzes the cleavage of NAD and the covalent linkage of ADP-ribose to elongation factor 2 (EF-2) resulting in the inhibition of protein synthesis (Bacha et al. (1983) J. Biol. Chem. 258:1565). To evaluate the mechanism by which $DAB_{486}EGF$ inhibits protein synthesis, A431 cells were plated in triplicate wells of 24 well plates containing DT, $DAB_{486}EGF$, or complete medium. Following a 20-hour incubation at 37° C., the cells were washed and incubated in lysis buffer (10 mM Tris, 10 mM NaCl, 3 mM Mg $Cl_2$, 10 mM thymidine, 1 mM EGTA, 1% TRITON X-100) with [$^{32}P$]NAD in the presence of purified DT fragment A (Calbiochem). TCA precipitable extracts were collected on glass fiber filters and counted to quantitate the percent of control EF-2 available for ADP-ribosylation. The results of these experiments are shown in Table 6. $DAB_{486}EGF$, like DT, reduced (in a dosage dependent manner) the amount of EF-2 available for ADP ribosylation.

TABLE 6

ADP-Ribosylation of EF-2 by $DAB_{486}EGF$

| Toxin | Concentration | Percent of Control Level of EF-2 Available for ADP-ribosylation |
|---|---|---|
| DT | $10^{-8}$ M | <1 |
|  | $10^{-9}$ M | 17 |
| $DAB_{486}EGF$ | $10^{-8}$ M | 13 |
|  | $10^{-9}$ M | 20 |

$DAB_{389}$ EGF Is An Improved Chimeric Toxin. $DAB_{389}EGF$ is far more toxic than is $DAB_{486}EGF$. As shown in FIGS. 8 and 9, $DAB_{389}EGF$ exhibits an $IC_{50}$ for the inhibition of protein synthesis in A431 cells approximately 10 times lower than that of $DAB_{486}EGF$ ($DAB_{389}EGF$ $IC_{50}=3\times 10^{-13}$M; $DAB_{486}EGF$ $IC_{50}=3\times 10^{-12}$M).

Figure 12:
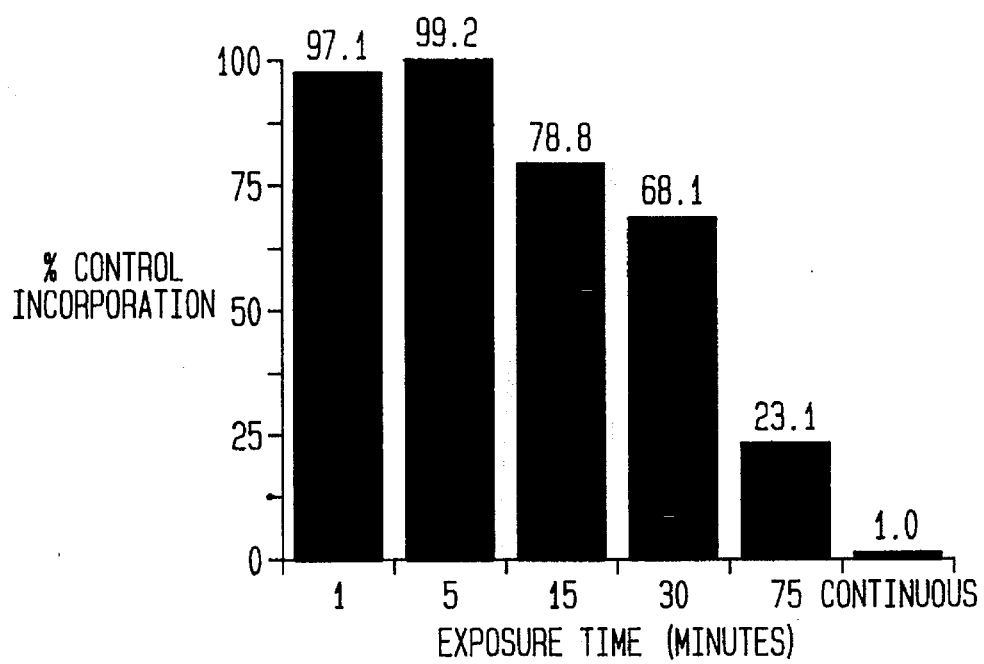
FIG. 12 is a graph of the effect of length of exposure to $DAB_{486}$EGF on the inhibition of protein synthesis.
Figure 13:
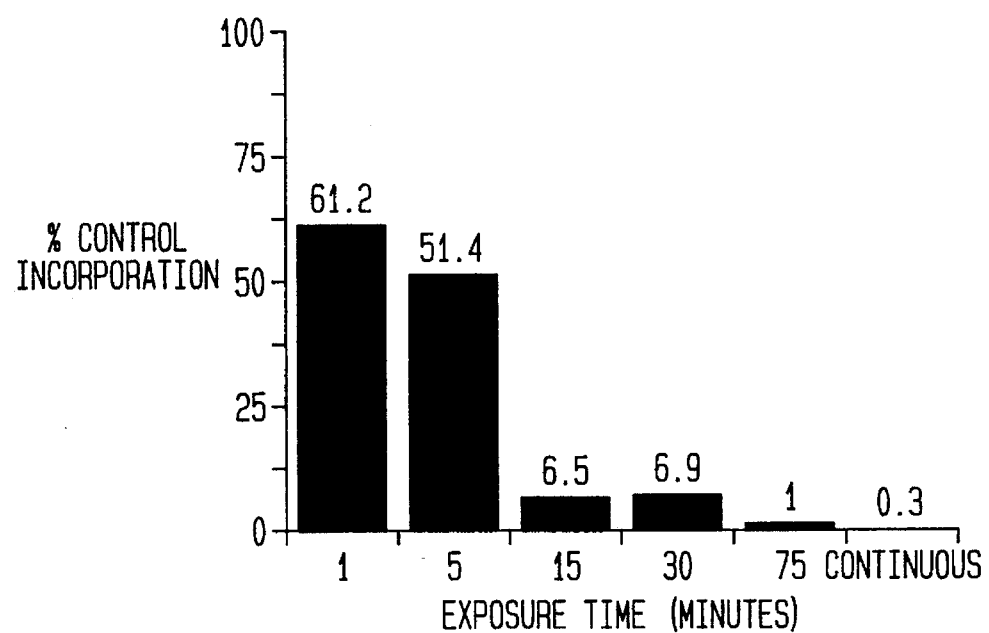
FIG. 13 is a graph of the effect of length of exposure to $DAB_{389}$EGF on the inhibition of protein synthesis.

The greater potency of $DAB_{389}EGF$ is also shown in experiments measuring the rapidity with which $DAB_{389}EGF$ and $DAB_{486}EGF$ kill A431 cells. FIGS. 12 and 12 show the exposure time (of A431 cells to $DAB_{486}EGF$ or $DAB_{389}EGF$) required to induce maximal inhibition of protein synthesis. Cells were exposed to $DAB_{486}EGF$ ($5\times 10^{-9}$M) (FIG. 12) or $DAB_{389}EGF$ ($5\times 10^{-9}$M) (FIG. 13) for the indicated times and then washed of unbound $DAB_{486}EGF$ or $DAB_{389}EGF$. Following an overnight incubation in complete media (DMEM+10% FCS), the cells were labeled with [$^{14}C$]leucine. The results show that near maximal inhibition of protein synthesis occurs following a 15-minute exposure to $DAB_{389}EGF$ while a greater than 75-minute exposure is required for $DAB_{486}EGF$.

Figure 14:
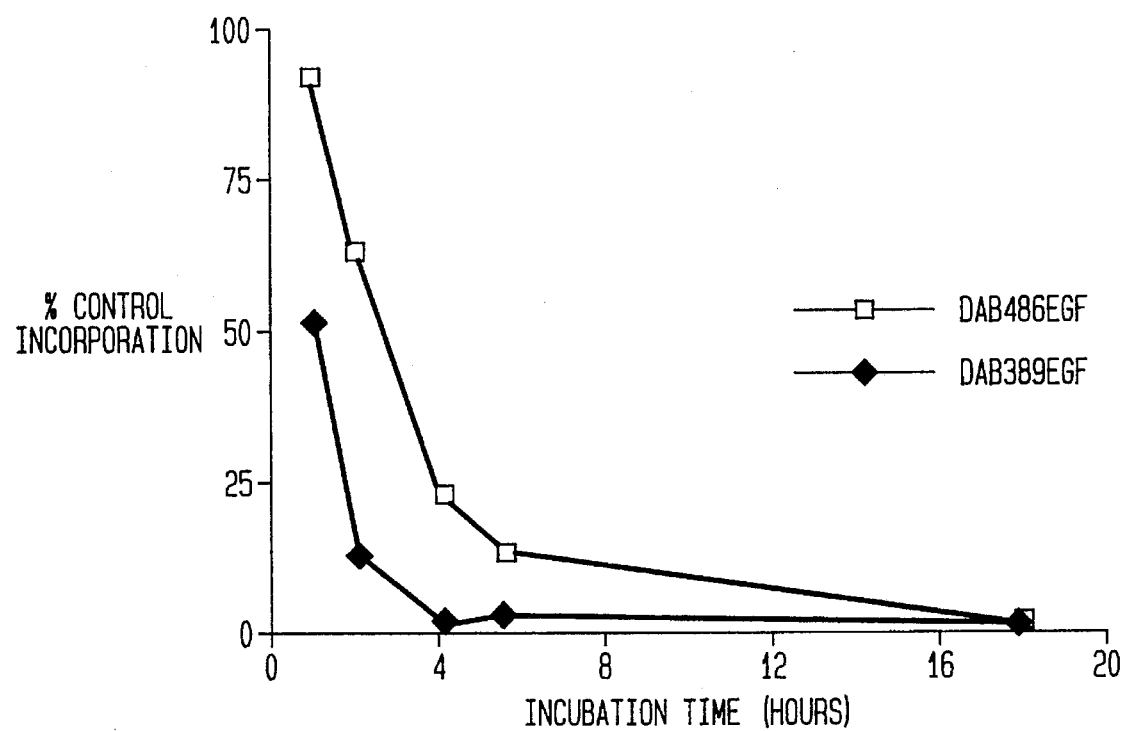
FIG. 14 is a graph of the kinetics of the inhibition of protein synthesis on cells incubated with $DAB_{486}$EGF or $DAB_{389}$EGF.

The kinetics of protein synthesis inhibition in $DAB_{389}EGF$ or $DAB_{486}EGF$ treated A431 cells is shown in FIG. 14. To examine the kinetics of protein synthesis inhibition A431 cells were incubated with $DAB_{486}EGF$ ($5\times 10^{-9}$) or $DAB_{389}EGF$ ($5\times 10^{-9}$M) in complete medium at 37° C. At the indicated times, $DAB_{486}EGF$ or $DAB_{389}EGF$ was removed and the cells were labeled with [$^{14}C$]leucine for 1 hour. The results indicate that there is a 50% reduction in protein synthesis following a 1-hour incubation with $DAB_{389}EGF$ while maximal inhibition occurs by 4 hours. Maximal inhibition of protein synthesis occurs more than 6 hours following incubation with $DAB_{486}EGF$.

Use

The improved chimeric toxins of the invention are administered to a mammal, e.g., a human, suffering from a medical disorder, e.g., cancer, or other conditions characterized by the presence of a class of unwanted cells to which a polypeptide ligand can selectively bind. The amount of protein administered will vary with the type of disease, extensiveness of the disease, and size of species of the mammal suffering from the disease. Generally, amounts will be in the range of those used for other cytotoxic agents used in the treatment of cancer, although in certain instances lower amounts will be needed because of the specificity and increased toxicity of the improved chimeric toxins.

The improved chimeric toxins can be administered using any conventional method; e.g., via injection, or via a timed-release implant. In the case of MSH improved chimeric toxins, topical creams can be used to kill primary cancer cells, and injections or implants can be used to kill metastatic cells. The improved chimeric toxins can be combined with any non-toxic, pharmaceutically-acceptable carrier substance.

Other Embodiments

Other embodiments are within the following claims. For example, chimeric toxins have been constructed, by methods known to those skilled in the art, in which $DAB_{389}$ and $DAB_{486}$ have been fused to interleukin 4 (IL-4). $DAB_{389}$-IL-4 is about 10 times more cytotoxic than is $DAB_{486}$-IL-4. $DAB_{389}$ has also been fused to interleukin 6. $DAB_{486}$ and $DAB_{389}$ have also been fused to human chorionic gonadotropin. The improved chimeric toxins of the invention include portions of DT fused to any cell-specific polypeptide ligand which has a binding domain specific for the particular class of cells which are to be intoxicated. Polypeptide hormones are useful such ligands. Chimeric toxins, e.g., those made using the binding domain of α or β MSH, can selectively bind to melanocytes, allowing the construction of improved DT-MSH chimeric toxins useful in the treatment of melanoma. Other specific-binding ligands which can be used include insulin, somatostatin, interleukins I and III, and granulocyte colony stimulating factor. Other useful polypeptide ligands having cell-specific binding domains are follicle stimulating hormone (specific for ovarian cells), luteinizing hormone (specific for ovarian cells), thyroid stimulating hormone (specific for thyroid cells), vasopressin (specific for uterine cells, as well as bladder and intestinal cells), prolactin (specific for breast cells), and growth hormone (specific for certain bone cells). Improved chimeric toxins using these ligands are useful in treating cancers or other diseases of the cell type to which there is specific binding.

For a number of cell-specific ligands, the region within each such ligand in which the binding domain is located is now known. Furthermore, recent advances in solid phase polypeptide synthesis enable those skilled in this technology to determine the binding domain of practically any such ligand, by synthesizing various fragments of the ligand and testing them for the ability to bind to the class of cells to be labeled. Thus, the chimeric toxins of the invention need not include an entire ligand, but rather may include only a fragment of a ligand which exhibits the desired cell-binding capacity. Likewise, analogs of the ligand or its cell-binding region having minor sequence variations may be synthesized, tested for their ability to bind to cells, and incorporated into the hybrid molecules of the invention. Other potential ligands include monoclonal antibodies or antigen-binding, single-chain analogs of monoclonal antibodies, where the antigen is a receptor or other moiety expressed on the surface of the target cell membrane.

What is claimed is:

1. A chimeric toxin which binds selectively to a predetermined class of cells, comprising protein fragments joined together by peptide bonds, said chimeric toxin comprising, sequentially from N-terminus to C-terminus, (a) a first fragment which is the enzymatically active fragment A of native diphtheria toxin and the $1_1$ cleavage domain of native diphtheria toxin;

(b) a second fragment comprising at least a portion of the hydrophobic transmembrane region of native diphtheria toxin effective to deliver said fragment A into the cytosol of the predetermined class of cells;

(c) a third fragment comprising the sequence of native diphtheria toxin fragment B amino acids C-terminal to the hydrophobic transmembrane region of native diphtheria toxin which is amino acids 372–535, minus the generalized eucaryotic binding domain of native diphtheria toxin which is amino acids 486–535, and minus the $1_2$ cleavage domain of native diphtheria toxin which are amino acids 461–471, and further minus at least 50 native diphtheria toxin amino acids between amino acid residue 386 of native diphtheria toxin and the generalized eucaryotic binding site of native diphtheria toxin, provided that the $1_2$ domain and the at least 50 amino acids deleted total no more than 99 amino acids; and (d) a fourth fragment comprising at least a portion of the binding domain of a cell-specific polypeptide ligand effective to cause said chimeric toxin to bind selectively to the predetermined class of cells which bear a receptor to the ligand;

wherein said chimeric toxin possesses greater toxicity to the predetermined class of cells than that of a toxin comprising $DAB_{486}$ fused to said fourth fragment.

2. A chimeric toxin according to claim 1, wherein said third fragment comprises the sequence of native diphtheria toxin fragment B amino acids C-terminal to the hydrophobic transmembrane region of native diphtheria toxin which is amino acids 372–535, minus the generalized eucaryotic binding domain of native diphtheria toxin which are amino acids 486–535, and minus the $1_2$ cleavage domain of native diphtheria toxin which is amino acids 461–471, and further minus at least 80 native diphtheria toxin amino acids between amino acid residue 386 of native diphtheria toxin and the generalized eucaryotic binding site of native diphtheria toxin, provided that the $1_2$ domain and the at least 80 amino acids deleted total no more than 99 amino acids.

3. A chimeric toxin according to claim 1, wherein said third fragment further comprises amino acid residues $His_{484}$ and $Ala_{485}$ of native diphtheria toxin.

4. A chimeric toxin according to claim 1, which lacks any diphtheria toxin amino acids C-terminal to amino acid residue 386 of native diphtheria toxin.

5. A chimeric toxin according to claim 1, wherein the length and composition of said third fragment render said chimeric toxin at least about four times as toxic to the predetermined class of cells as $DAB_{486}$ fused to said fourth fragment.

6. A chimeric toxin according to claim 1, wherein the length and composition of said third fragment render said chimeric toxin at least about 10 times as toxic to the predetermined class of cells as $DAB_{486}$ fused to said fourth fragment.

7. A chimeric toxin according to claim 1, wherein said fourth fragment comprises a portion of the binding domain of EGF effective to cause said chimeric toxin to bind selectively to the predetermined class of cells which bear a receptor to EGF.

8. A chimeric toxin according to claim 7, wherein said fourth fragment comprises EGF.

9. A chimeric toxin according to claim 1, wherein said fourth fragment comprises at least a portion of the binding domain of IL-2 effective to cause said chimeric toxin to bind selectively to the predetermined class of cells which bear a receptor to IL-2.

10. A chimeric toxin according to claim 9, wherein said fourth fragment comprises amino acids 2 to 133 of human IL-2.

11. A chimeric toxin according to claim 1, wherein said fourth fragment comprises at least a portion of the binding domain of IL-4 effective to cause said chimeric toxin to bind selectively to the predetermined class of cells which bear a receptor to IL-4.

12. A chimeric toxin according to claim 11, wherein said fourth fragment comprises IL-4.

13. A chimeric toxin according to claim 1, wherein fourth fragment comprises at least a portion of the binding domain of IL-6 effective to cause said chimeric toxin to bind selectively to the predetermined class of cells which bear a receptor to IL-6.

14. A chimeric toxin according to claim 13, wherein said fourth fragment comprises IL-6.

15. A chimeric toxin which binds selectively to a predetermined class of cells, comprising protein fragments joined together by peptide bonds, said chimeric toxin comprising, sequentially from N-terminus to C-terminus, (a) a first fragment which is the enzymatically active fragment A of native diphtheria toxin and the $1_1$ cleavage domain of native diphtheria toxin;

(b) a second fragment comprising at least a portion of the hydrophobic transmembrane region of native diphtheria toxin effective to deliver said fragment A into the cytosol of the predetermined class of cells;

(c) a third fragment comprising the sequence of native diphtheria toxin fragment B amino acids C-terminal to the hydrophobic transmembrane region of native diphtheria toxin which is amino acids 372–535, minus the generalized eucaryotic binding domain of native diphtheria toxin which is amino acids 486–535, and minus a sequence of from 61 to 99 native diphtheria toxin amino acids, which includes the $1_2$ region of native diphtheria toxin which is amino acids 461–471, the deleted sequence being N-terminal with respect to the generalized eucaryotic binding site of native diphtheria toxin and C-terminal with respect to amino acid residue 386 of native diphtheria toxin; and (d) a fourth fragment comprising at least a portion of the binding domain of a cell-specific polypeptide ligand effective to cause said chimeric toxin to bind selectively to the predetermined class of cells which bear a receptor to said ligand;

wherein said chimeric toxin possesses greater toxicity to the predetermined class of cells than that of a toxin comprising $DAB_{486}$ fused to said fourth fragment.

16. A chimeric toxin according to claim 15, wherein said third fragment further comprises amino acid residues $His_{484}$ and $Ala_{485}$ of native diphtheria toxin.

17. A chimeric toxin according to claim 16, wherein the deleted sequence of from 61 to 97 native diphtheria toxin amino acids is immediately N-terminal to amino acid residue $His_{484}$ of native diphtheria toxin.

18. A chimeric toxin according to claim 17, wherein the sequence deleted contains from 80 to 97 native diphtheria toxin amino acids.

19. A chimeric toxin according to claim 18, wherein the deleted sequence contains 97 amino acids.

20. A chimeric toxin according to claim 19, wherein said first, second, and third fragments together consist of $DAB_{389}$.

21. A chimeric toxin according to claim 15, which lacks any diphtheria toxin amino acids C-terminal to amino acid residue 386 of native diphtheria toxin.

22. A chimeric toxin according to claim 15, wherein the length and composition of said third fragment render said chimeric toxin at least about four times as toxic to the predetermined class of cells as $DAB_{486}$ fused to said fourth fragment.

23. A chimeric toxin according to claim 15, wherein the length and composition of said third fragment render said chimeric toxin at least about 10 times as toxic to the predetermined class of cells as $DAB_{486}$ fused to said fourth fragment.

24. A chimeric toxin according to claim 15, wherein said fourth fragment comprises a portion of the binding domain of EGF effective to cause said chimeric toxin to bind selectively to the predetermined class of cells which bear a receptor to EGF.

25. A chimeric toxin according to claim 24, wherein said fourth fragment comprises EGF.

26. A chimeric toxin according to claim 15, wherein said fourth fragment comprises at least a portion of the binding domain of IL-2 effective to cause said chimeric toxin to bind selectively to the predetermined class of cells which bear a receptor to IL-2.

27. A chimeric toxin according to claim 26, wherein said fourth fragment comprises amino acids 2 to 133 of human IL-2.

28. A chimeric toxin according to claim 15, wherein said fourth fragment comprises at least a portion of the binding domain of IL-4 effective to cause said chimeric toxin to bind selectively to the predetermined class of cells which bear a receptor to IL-4.

29. A chimeric toxin according to claim 28, wherein said fourth fragment comprises IL-4.

30. A chimeric toxin according to claim 15, wherein fourth fragment comprises at least a portion of the binding domain of IL-6 effective to cause said chimeric toxin to bind selectively to the predetermined class of cells which bear a receptor to IL-6.

31. A chimeric toxin according to claim 30, wherein said fourth fragment comprises IL-6.

32. The chimeric toxin, which is $DAB_{389}$-IL-2(2–133).

33. The chimeric toxin, which is $DAB_{389}$-EGF.

* * * * *

UNITED STATES PATENT AND TRADEMARK OFFICE
CERTIFICATE OF CORRECTION

PATENT NO. : 5,616,482
DATED : April 1, 1997
INVENTOR(S) : Williams

Page 1 of 3

It is certified that error appears in the above-identified patent and that said Letters Patent is hereby corrected as shown below:

Title page item [76] Inventor, please add --John R. Murphy--.

In the Abstract: line 2, delete "." and insert --, the chimeric toxin comprising, in sequential order, beginning at the amino terminal end of the chimeric toxin,
    (a) the enzymatically active Fragment A of diphtheria toxin,
    (b) a first fragment including the cleavage domain $l_1$ adjacent the Fragment A of diphtheria toxin,
    (c) a second fragment comprising at least a portion of the hydrophobic transmembrane region of Fragment B of diphtheria toxin, the second fragment having a deletion of at least 50 diphtheria toxin amino acid residues, the deletion being C-terminal to the portion of the transmembrane region, and the second fragment not including domain $l_2$, and
    (d) a third fragment comprising a portion of a cell-specific polypeptide ligand, the portion including at least a portion of the binding domain of the polypeptide ligand, the portion of the binding domain being effective to cause the chimeric toxin to bind selectively to a predetermined class of cells to be attacked by the enzymatically active Fragment A, the chimeric toxin possessing any of, greater toxicity than that of a toxin comprised of $DAB_{486}$ fused to the third fragment, a lower $K_d$ for the sites on cells of the predetermined class to which the chimeric toxin binds than that of a toxin comprised of $DAB_{486}$ fused to the third fragment, greater resistance to proteolytic degradation than that exhibited by a toxin comprised of $DAB_{486}$ fused to the third fragment, greater resistance to the inhibition of its cytotoxicity by the cell-specific polypeptide ligand than that exhibited by $DAB_{486}$ fused to the third fragment, the ability to inhibit protein synthesis to a given degree by a period of exposure that is shorter than the period of exposure required by $DAB_{489}$ fused to the third fragment to

UNITED STATES PATENT AND TRADEMARK OFFICE
CERTIFICATE OF CORRECTION

PATENT NO. : 5,616,482
DATED : April 1, 1997
INVENTOR(S) : Williams

It is certified that error appears in the above-identified patent and that said Letters Patent is hereby corrected as shown below:

inhibit protein synthesis to the same degree, or the ability to effect a more rapid onset of the inhibition of protein synthesis than that exhibited by $DAB_{486}$ fused to the third fragment.--
Column 1, line 22, "chimetic" should read --chimeric--
Column 1, line 50, "chimetic" should read --chimeric--
Column 2, line 39, "chimetic" should read --chimeric--
Column 3, line 28, "size" should read --site--
Column 3, line 37, "$DAB_{489}$" should read --$DAB_{486}$--
Column 4, line 26, "are a diagram" should read --are diagrams--
Column 9, lines 15-16, "$1X10^-{}_{10}M$" should read --$1X10^{-10}M$--
Column 9, lines 54-55, "$Kd=2.5X10^-{}_{8}M$)." should read --$Kd=2.5X10^{-8}M$).--
Column 11, line 30, "HindIIi" should read --HindIII--
Column 14, line 66, "quantirate" should read --quantitate--
Column 15, line 2, "dosace" should read --dosage--
Column 15, lines 21-22, "$IC_{50}=3X10^-{}_{12}M$)." should read --$IC_{50}=3X10^{-12}M$).--

UNITED STATES PATENT AND TRADEMARK OFFICE
CERTIFICATE OF CORRECTION

PATENT NO. : 5,616,482
DATED : April 1, 1997
INVENTOR(S) : Williams

It is certified that error appears in the above-identified patent and that said Letters Patent is hereby corrected as shown below:

Column 15, lines 40-41, "$(5X10^-_9)$" should read --$(5X10^{-9})$--
Column 17, line 6, "are" should read --is--
Column 17, line 26, "are" should read --is--

Signed and Sealed this

Seventeenth Day of March, 1998

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,616,482  
DATED : April 1, 1997  
INVENTOR(S) : Diane P. Williams and John R. Murphy Page 1 of 1

It is certified that error appears in the above-identified patent and that said Letters Patent is hereby corrected as shown below:

Column 1,
Line 2, please insert:
-- GOVERNMENT INTERESTS
This invention was made in the course of work supported by the U.S. Government. The Government has certain rights to this invention. --.

Signed and Sealed this

Twenty-ninth Day of November, 2005

JON W. DUDAS
*Director of the United States Patent and Trademark Office*